(12) United States Patent
Laufer et al.

(10) Patent No.: US 7,629,140 B2
(45) Date of Patent: Dec. 8, 2009

(54) ASSAY FOR CYTOCHROME P450 ISOFORM 2C9

(75) Inventors: Ralph Laufer, Rome (IT); Annalise Di Marco, Rieti (IT); Ashok Chaudhary, Matawan, NJ (US)

(73) Assignee: Istituto di Richerche di Biologia Molecolare P. Angeletti S.p.A., Pomezia, Rome (IT)

( * ) Notice: Subject to any disclaimer, the term of this patent is extended or adjusted under 35 U.S.C. 154(b) by 277 days.

(21) Appl. No.: 11/663,587

(22) PCT Filed: Oct. 4, 2005

(86) PCT No.: PCT/US2005/035688

§ 371 (c)(1), (2), (4) Date: Mar. 23, 2007

(87) PCT Pub. No.: WO2006/041844

PCT Pub. Date: Apr. 20, 2006

(65) Prior Publication Data

US 2008/0193950 A1    Aug. 14, 2008

Related U.S. Application Data

(60) Provisional application No. 60/616,943, filed on Oct. 7, 2004.

(51) Int. Cl.
*C12Q 1/26* (2006.01)

(52) U.S. Cl. .......................................... 435/25; 435/69.2

(58) Field of Classification Search ................ 435/69.2, 435/25
See application file for complete search history.

(56) References Cited

U.S. PATENT DOCUMENTS

| | | | |
|---|---|---|---|
| 6,338,802 B1 | 1/2002 | Bodner et al. | |
| 6,491,873 B2 | 12/2002 | Roberts et al. | |
| 6,506,343 B1 | 1/2003 | Bodner et al. | |
| 6,726,842 B2 | 4/2004 | Bouvier et al. | |
| 2003/0143124 A1 | 7/2003 | Roberts et al. | |
| 2003/0195350 A1 | 10/2003 | Leyland-Jones | |
| 2004/0043377 A1 | 3/2004 | Shimada et al. | |
| 2008/0145886 A1* | 6/2008 | Laufer et al. .................. | 435/27 |

FOREIGN PATENT DOCUMENTS

| | | | |
|---|---|---|---|
| WO | WO 97/38774 | | 10/1997 |
| WO | WO 2005/098025 | * | 10/2005 |

OTHER PUBLICATIONS

Sioufi A. et al. Determination of Diclofenac in Plasma and Urine . . . J of Chromatography 571:87-100, 1991.*
Bachmann et al., Current Drug Metab . . . , vol. 2 (2001), pp. 299-314, "The use of in vitro methods to predict in vivo pharmacokinetics . . . ".
Bourrie et al., J. Pharmacol. & Exper. Ther., vol. 277 (1996), pp. 321-332, "Cytochrome P450 isoform inhibitors as a tool for the investigation . . . ".
Cohen et al., Drug Metab. & Disposition, vol. 31 (2003), pp. 1005-1015, "In vitro drug interactions of cytochrome P450: an evaluation . . . ".
Crespi et al., J. Pharmacol. & Toxicol. Methods, vol. 44 (2000), pp. 325-331, "Fluorometric screening for metabolism-based drug-drug interactions".
Eagling et al., Br. J. Clin. Pharmacol., vol. 45 (1998), pp. 107-114, "Differential selectivity of cytochrome P450 inhibitors against probe substrates . . . ".
Egnell et al., J. Pharmacol. & Exper. Ther., vol. 307 (2003), pp. 878-887, "Generation and evaluation of a CYP2C9 heteroactivation pharmacophore".
Goldstein et al., Br. J. Clin. Pharmacol., vol. 52 (2001), pp. 349-355, "Clinical relevance of genetic polymorphisms in the human CYP2C subfamily".
Hengstler et al., Drug Metab. Rev., vol. 32, pp. 81-118, "Cryopreserved oprimary hepatocytes as a constantly available in vitro model . . . ".
Hummel et al., Biochemistry, vol. 43 (2004), pp. 7207-7214, "Effector-mediated alteration of substrate orientation in cytochrome P450 2C9".
Hutzler et al., Arch. Biochemistry & Biophysics, vol. 410 (2003), pp. 16-34, "Activation of cytochrome P450 2C9-mediated metabolism: . . . ".
Ito et al., Br. J. Clin. Pharmacol., vol. 57 (2004), pp. 473-486, "Database analyses for the prediction of in vivo drug-drug interactions from in vitro data".
Korzekwa et al., Biochemistry, vol. 37 (1998), pp. 4137-4147, "Evaluation of atypical cytochrome P450 kinetics with two-substrate models: evidence that multiple substrates . . . ".
Lin et al., Clin. Pharmacokinet., vol. 34 (1998), pp. 361-390, "Inhibition and induction of cytochrome P450 and the clinical implications".
Mei et al., J. Pharmacol. & Exper. Ther., vol. 291 (1999), pp. 749-759, "Role of a potent inhibitory monoclona antibody cytochrome P-450 3A4 . . . ".
Miners et al., Br. J. clin. Pharmacol., vol. 45 (1998), pp. 525-538, "Cytochrome P4502C9: an enzyme of major importance in human drug . . . ".

(Continued)

*Primary Examiner*—Ralph Gitomer
(74) *Attorney, Agent, or Firm*—John David Reilly; Catherine D. Fitch

(57) ABSTRACT

A Rapid And Sensitive Radiometric Assay For Assessing The Activity Of Cytochrome P-450 (CYP) 2C9 And The Potential Of An Analyte To Inhibit CYP2C9 Activity Or Induce CYP2C9 Expression is described. All the steps of the assay, including incubations, product separation, and radioactivity counting are preferably performed in a multiwell format, which can be automated.

8 Claims, 14 Drawing Sheets

OTHER PUBLICATIONS

Moser et al., J. Med. Chem., vol. 33 (1990), pp. 2358-2368, "Synthesis and quantitative structure—activity relationships . . .".

Oza et al., J. Med. Chem., vol. 45 (2002), pp. 321-332, "Synthesis, structure, and activity of diclofenac analgoues as . . .".

Satoh et al., J. Med. Chem., vol. 36 (1993), pp. 3580-3594, "Substituted chromenes as potent, orally active 5-lipoxygenase . . .".

Schwarz, Eur. J. Clin. Investig., vol. 33 (2003), pp. 23-30, "Clinical relevance of genetic polymorphisms in the human CyP2C9 gene".

Shou et al., Eur. J. Pharmacol., vol. 394 (2000), pp. 199-209, "Use of inhibitory monoclonal antibodies to assess the contribution of cytochromes P450 . . .".

von Moltke et al., Biochem. Pharmacol., vol. 55 (1998), pp. 113-122, "In vitro approaches to predicting drug interactions in vivo".

Xie et al., Adv. Drug Delivery Rev., vol. 54 (2002), pp. 1257-1270, "CYP2C9 allelic variants: ethnic distribution an functional . . .".

Riley, Curr. Opin. in Drug Discovery & Develop., vol. 4 (2001), pp. 45-54, "The potential pharmacological an toxicological impact . . .".

Thummel et al., Ann. Rev. Pharmacol. Toxicol., vol. 38 (1998), pp. 389-430, "In vitro and in vivo drug interadtions involving human CYP3A".

Guengerich, Cytochromes P450: Metabolic & Toxicological Aspects, Chapter 3, pp. 55-74, "The chemistry of cytochrome P450 reactions".

Ioannides et al., Cytochromes P450: Metabolic & Toxicological Aspects, Chapter 12, pp. 301-327, "Expression of cytochrome P450 proteins in disease".

Lewis, Cytochromes P450: Metabolic & Toxicological Aspects, Chapter 14, pp. 355-398, "Molecular modeling of mammalian cytochromes P450".

Dich et al., Methods in Molecular Biology, vol. 5: Animal Cell Culture (1989), pp. 161-176, "Primary cultures of rat hepatocytes".

Bertz et al., Clin. Pharmacokinet., vol. 32 (1997), pp. 210-258, "Use of in vitro and in vivo data to estimate the likelihood of metabolic . . .".

Guengerich, Ann. Rev. Pharmacol. & Toxicology, vol. 39 (1999), pp. 1-17, "Cytochrome P-450 3A4: Regulation and role in drug metabolism".

Northrop, Meth. Enzymol., vol. 87 (1982), pp. 607-625, "Deuterium and tritium isotope effects on initial rates".

Ferrini et al., Methods in Molec. Biol., vol. 107: Cytochrome P450 Protocols (1998), pp. 341-352, Human hepatocyte culture.

De Lean et al., The Receptors: A Comprehensive Treatise, vol. 1 (1979), p. 143-192, "Kinetics of cooperative binding".

* cited by examiner

ASSAY FOR CYTOCHROME P450 ISOFORM 2C9

CROSS-REFERENCE TO RELATED APPLICATIONS

This patent application claims benefit of International Patent Application No. PCT/US2005/035688, which was filed 4 Oct. 2005, and U.S. Provisional application No. 60/616,943, which was filed 7 Oct. 2004.

BACKGROUND OF THE INVENTION (1) Field of the Invention

The present invention relates to an assay for assessing the activity of CYP2C9 and the potential of an analyte to modulate CYP2C9 activity, e.g., inhibitor or inducer of CYP2C9 activity. The assay determines CYP2C9 activity by measuring 4'-hydroxylation of diclofenac in reactions comprising CYP2C9, microsomes comprising CYP2C9, or hepatocytes using diclofenac labeled with tritium in the 4' position as a substrate and a sorbent which preferentially binds non-polar compounds such as diclofenac to separate the labeled diclofenac from tritiated water formed during hydroxylation of the labeled diclofenac at the 4' position by CYP2C9. The assay is useful for assessing CYP2C9 enzymatic activity and CYP2C9 inhibition or induction potential of drug candidates in order to exclude potent CYP inhibitors or inducers from further development.

(2) Description of Related Art

The pharmacokinetic and toxicokinetic properties of pharmaceuticals depend in great part on their biotransformation by drug metabolizing enzymes. The main drug metabolizing system in mammals is cytochrome P450 (CYP), a family of microsomal enzymes present predominantly in the liver. Multiple isoforms of CYP catalyze the oxidation of chemicals of endogenous and exogenous origin, including drugs, steroids, prostanoids, eicosanoids, fatty acids, and environmental toxins (Ioannides, In Cytochromes P450. Metabolic and Toxicological Aspects. CRC Press, Boca Raton. (1996)). If a drug that is metabolized by a particular CYP isozyme is co-administered with an inhibitor of that same enzyme, changes in its pharmacokinetics can occur, which can give rise to adverse effect (Bertz and Granneman, Clin. Pharmacokinet. 32: 210-258 (1997); Lin and Lu, Clin. Pharmacokinet. 35: 361-390 (1998); Thummel and Wilkinson, Ann. Rev. Pharmacol. Toxicol. 38: 389-430 (1998); von Moltke et al., Biochem. Pharmacol. 55: 113-122 (1998)). It is therefore important to be able to predict and to prevent the occurrence of clearance changes due to metabolic inhibition. During the drug discovery process, it is routine practice in the pharmaceutical industry to assess CYP inhibition potential of drug candidates in order to exclude potent inhibitors from further development (Lin and Lu, ibid. (1998); Crespi and Stresser, J. Pharmacol. Toxicol. Methods 44: 325-331 (2000); Bachmann and Ghosh, Curr. Drug Metab. 2: 299-314 (2001); Riley, Curr. Opin. Drug Disc. Dev. 4: 45-54 (2001)).

The polymorphically expressed CYP2C9 is one of the most important drug metabolizing enzymes in humans. It constitutes about 20% of the total human liver CYP content and metabolizes about 10% of therapeutically important drugs (Miners and Birkett, Br. J. Pharmacol. 45: 525-538 (1998); Goldstein, Br. J. Clin. Pharmacol. 52: 349-355 (2001); Xie et al., Adv. Drug Deliv. Rev. 54: 1257-1270 (2002); Schwarz, Eur. J. Clin. Invest. 33: 23-30 (2003)). Many clinically relevant drug interactions due to inhibition of CYP2C9 have been described (Miners and Birkett, ibid.; Ito et al., Br. J. Clin. Pharmacol. 57: 473-486 (2004)). Several assay methods are currently used for determining the potential of drug candidates to inhibit CYP2C9 activity, and each of these methods presents distinct advantages and disadvantages. The most widely used marker reactions are diclofenac 4'-hydroxylation, tolbutamide 4'-hydroxylation, and S-warfarin 7'-hydroxylation. Inhibition assays are typically conducted using human liver microsomes (HLM) as the enzyme source and high pressure liquid chromatography (HPLC) with ultraviolet (UV) or mass spectrometric (MS) detection for quantifying the hydroxylated substrate.

Because of the need to use HPLC to isolate and detect the hydroxylated substrate, current assays for detecting inhibitors of CYP2C9 are not suited for high throughput screening. In an attempt to create an assay that is suitable for high throughput screening, a number of fluorogenic substrate probes have been developed. These probes enable detection of the hydroxylated substrate by measuring fluorescence. There is no need to separate the product from the other components of the assay. The ability to detect the product without having to isolate the product by HPLC provides an assay practical for use in a high throughput screening format. However, using fluorogenic probes have several disadvantages. First, the fluorogenic probes are frequently metabolized by more than one CYP isoform; therefore, the assays have to be conducted using a single CYP isoform (produced by recombinant DNA technology) instead of HLM. Second, the results of assays that use the fluorogenic probes and a recombinant CYP isoform do not correlate well with results obtained using conventional probes in HLM (Cohen et al. Drug Metab. Dispos. 31, 1005 (2003)). The reason for the lack of correlation may include metabolism of test inhibitors by enzymes present in the HLM but not in assays that use a recombinant CYP isoform and the existence of multiple substrate binding sites.

Therefore, there remains a need for an assay for identifying CYP2C9 modulators that is based on using diclofenac as the substrate, is at least as sensitive and specific as the conventional assays, and is readily adaptable to a high throughput screening format. There is also a need for an assay for assessing CYP2C9 activity in hepatocytes.

BRIEF SUMMARY OF THE INVENTION

The present invention provides a rapid and sensitive radiometric assay for assessing the activity of cytochrome P-450 isoform 2C9 (CYP2C9) and the potential of an analyte to inhibit or induce CYP2C9 activity. The assay is based on detecting the release of tritium as [$^3$H]—H$_2$O which occurs upon CYP2C9-mediated hydroxylation of diclofenac labeled with tritium in the 4' position ([4'$^3$H]-diclofenac) in the presence of the analyte wherein an increase in the release of tritium over time in hepatocytes in the presence of an analyte or a decrease in the release of tritium over time in reactions comprising CYP2C9 in the presence of an analyte indicates that the analyte is a modulator of CYP2C9 activity. The method further enables CYP2C9 activity in hepatocyte preparations to be determined. In contrast to conventional diclofenac 4'-hydroxylation assays, the assay herein does not require HPLC separation and mass spectrometry. Instead, the tritiated water product is separated from tritiated diclofenac in a solid-phase extraction process using a sorbent which preferentially binds non-polar compounds such as diclofenac. All the steps of the assay, including incubations, product separation, and radioactivity counting are preferably performed in a multiwell format, which can be automated.

Therefore, in one embodiment, the present invention provides a method for identifying an analyte that inhibits activity of CYP2C9, which comprises providing an aqueous mixture comprising CYP2C9, tritium-labeled diclofenac labeled with tritium at the 4' position, NADPH, optionally an NADPH regenerating system, and the analyte; incubating the aqueous mixture for a time sufficient for the CYP2C9 to hydroxylate the tritium-labeled diclofenac at the 4' position, which produces tritium-labeled water; optionally removing the CYP2C9 from the aqueous mixture; applying the aqueous mixture to a sorbent which preferentially binds non-polar compounds such as diclofenac to remove the tritium-labeled diclofenac from the aqueous mixture; and, measuring amount of the tritium-labeled water in the aqueous mixture with the tritium-labeled diclofenac removed wherein a decrease in the amount of the tritium-labeled water in the presence of the analyte compared to the amount of the tritium-labeled water in the absence of the analyte indicates that the analyte inhibits activity of the CYP2C9.

In a further aspect of the above embodiment, the sorbent comprises a water-wettable polymer formed by copolymerizing at least one hydrophilic monomer and at least one lipophilic monomer in a ratio sufficient for the polymer to be water-wettable and effective at retaining organic solutes thereon. In further aspects of the above embodiment, the lipophilic monomer comprises a phenyl, phenylene, ether, or $C_2$-$C_{18}$ alkyl group. In a further still aspect, the lipophilic monomer is divinylbenzene. In further aspects of the above embodiments, the hydrophilic monomer comprises a saturated, unsaturated, or aromatic heterocyclic group. In a further still aspect, the hydrophilic monomer is N-vinylpyrrolidone. In further still aspects of the above embodiment, the water wettable polymer is poly(vinylbenzene-co-N-vinylpyrrolidone), preferably, a polymer wherein the poly(vinylbenzene-co-N-vinylpyrrolidone)comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In another aspect of the above embodiment, the sorbent comprises a non-polar group bonded to a silica substrate. In a further still aspect, the sorbent comprises one or more silanes selected from the group consisting phenyl silane, dimethylsilane, trimethylsilane, ethyl silane, butyl silane, hexyl silane, octyl silane, and octadecyl silane. In further still aspects, the silica substrate is selected from the group consisting of silica particles and silica gel.

In a further still embodiment, the sorbent comprises activated charcoal.

In a further still embodiment, the present invention provides a method for identifying an analyte that inhibits activity of CYP2C9, which comprises providing a mixture comprising CYP2C9, tritium-labeled diclofenac labeled with tritium solely at the 4' position, NADPH, optionally an NADPH regenerating system, and the analyte; incubating the mixture for a time sufficient for the CYP2C9 activity to hydroxylate the tritium-labeled diclofenac at the 4' position, optionally removing the CYP2C9 from the mixture; applying the mixture to a water-wettable polymer formed by copolymerizing at least one hydrophilic monomer and at least one lipophilic monomer in a ratio sufficient for the polymer to be water-wettable and effective at retaining organic solutes thereon to remove the tritium-labeled diclofenac from the aqueous mixture; and, measuring amount of the tritium in the mixture with the tritium-labeled diclofenac removed wherein a decrease in the amount of the tritium in the presence of the analyte indicates that the analyte inhibits activity of the CYP2C9.

In further aspects of the above embodiment, the lipophilic monomer comprises a phenyl, phenylene, ether, or $C_2$-$C_{18}$ alkyl group. In a further still aspect, the lipophilic monomer is divinylbenzene.

In further aspects of the above embodiment, the hydrophilic monomer comprises a saturated, unsaturated, or aromatic heterocyclic group. In a further still aspect, the hydrophilic monomer is N-vinylpyrrolidone.

In further still aspects of the above embodiment, the water wettable polymer is poly(vinylbenzene-co-N-vinylpyrrolidone, preferably, a polymer wherein the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In a further embodiment, the present invention provides a method for identifying an analyte that inhibits activity of CYP2C9, which comprises providing a mixture comprising CYP2C9, tritium-labeled diclofenac labeled with tritium at the 4' position, NADPH, optionally an NADPH regenerating system, and the analyte; incubating the mixture for a time sufficient for the CYP2C9 activity to hydroxylate the tritium-labeled diclofenac at the 4' position; optionally removing the CYP2C9 from the mixture; applying the mixture to a water wettable polymer formed by copolymerizing divinylbenzene and N-vinylpyrrolidine at a ratio of divinylbenzene to N-vinylpyrrolidine such that the poly(vinylbenzene-co-N-vinylpyrrolidone) formed is water-wettable and effective at retaining organic solutes thereon to separate the human liver microsomes and tritium-labeled diclofenac from any tritium-labeled water in the mixture; and, measuring amount of the tritium in the aqueous mixture with the tritium-labeled diclofenac removed wherein a decrease in the amount of the tritium in the presence of the analyte indicates that the analyte inhibits activity of the CYP2C9.

In further aspects of the above embodiment, the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In further still embodiments of the above, the water wettable polymer is packed inside a solid phase extraction cartridge or column. In a particularly preferred embodiment of any one of the above, the method is performed in a multiwell plate format comprising a first multiwell plate for performing the incubation, a multicolumn plate in the same configuration as the multiwell plate for separating the labeled diclofenac from the tritiated water after the incubation, and a second multiwell plate for collecting the column void volume and washes from the multicolumn for determining the tritium therein.

The present invention further provides a method for identifying an analyte that inhibits activity of CYP2C9, which comprises providing a multiwell plate and a column plate having an array of solid phase extraction cartridges or columns having therein a sorbent which preferentially binds non-polar compounds such as diclofenac; applying to each of the wells of the multiwell plate a mixture comprising CYP2C9, tritium-labeled diclofenac labeled with tritium solely at the 4' position, and an analyte; contacting NADPH and optionally an NADPH regenerating system, to the mixture in each of the wells above and incubating for a time sufficient for the CYP2C9 to hydroxylate the tritium-labeled diclofenac at the 4' position; optionally separating the CYP2C9 from the mixture in each of the wells of the multiwell plate; applying each mixture to a separate minicolumn of the column plate to remove the tritium-labeled diclofenac from the mixture; and, measuring amount of the tritium in the mixture with the tritium-labeled diclofenac removed wherein a decrease in the amount of the tritium in the presence of the analyte indicates that the analyte inhibits activity of the CYP2C9.

In a further aspect of the above embodiment, the sorbent comprises a water-wettable polymer formed by copolymerizing at least one hydrophilic monomer and at least one lipophilic monomer in a ratio sufficient for the polymer to be water-wettable and effective at retaining organic solutes thereon. In further aspects of the above embodiment, the lipophilic monomer comprises a phenyl, phenylene, ether, or $C_2$-$C_{18}$ alkyl group. In a further still aspect, the lipophilic monomer is divinylbenzene. In further aspects of the above embodiments, the hydrophilic monomer comprises a saturated, unsaturated, or aromatic heterocyclic group. In a further still aspect, the hydrophilic monomer is N-vinylpyrrolidone. In further still aspects of the above embodiment, the water wettable polymer is poly(vinylbenzene-co-N-vinylpyrrolidone), preferably, a polymer wherein the poly(vinylbenzene-co-N-vinylpyrrolidone)comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In another aspect of the above embodiment, the sorbent comprises a non-polar group bonded to a silica substrate. In a further still aspect, the sorbent comprises one or more silanes selected from the group consisting phenyl silane, dimethylsilane, trimethylsilane, ethyl silane, butyl silane, hexyl silane, octyl silane, and octadecyl silane. In further still aspects, the silica substrate is selected from the group consisting of silica particles and silica gel.

The present invention further provides a method for identifying an analyte that inhibits activity of CYP2C9, which comprises providing a multiwell plate and a column plate having an array of solid phase extraction cartridges or columns having therein a water-wettable polymer formed by copolymerizing at least one hydrophilic monomer and at least one lipophilic monomer in a ratio sufficient for the polymer to be water-wettable and effective at retaining organic solutes thereon; applying to each of the wells of the multiwell plate a mixture comprising CYP2C9, tritium-labeled diclofenac labeled with tritium at the 4' position, and an analyte; contacting NADPH and optionally an NAPDH regenerating system to the mixture in each of the wells above and incubating for a time sufficient for the CYP2C9 to hydroxylate the tritium-labeled diclofenac at the 4' position; optionally separating the CYP2C9 from the mixture in each of the wells of the multiwell plate; applying each aqueous mixture to a separate minicolumn of the column plate to remove the tritium-labeled diclofenac from the mixture; and, measuring amount of the tritium in the mixture with the tritium-labeled diclofenac removed wherein a decrease in the amount of the tritium in the presence of the analyte indicates that the analyte inhibits activity of the CYP2C9.

In further aspects of the above embodiment, the lipophilic monomer comprises a phenyl, phenylene, ether, or $C_2$-$C_{18}$ alkyl group. In a further still aspect, the lipophilic monomer is divinylbenzene.

In further aspects of the above embodiments, the hydrophilic monomer comprises a saturated, unsaturated, or aromatic heterocyclic group; In a further still aspect, the hydrophilic monomer is N-vinylpyrrolidone.

In further still aspects of the above embodiment, the water wettable polymer is poly(vinylbenzene-co-N-vinylpyrrolidone), preferably, a polymer wherein the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In a further embodiment, the present invention provides a method for identifying an analyte that inhibits activity of CYP2C9, which comprises providing a multiwell plate and a column plate having an array of solid phase extraction cartridges or columns having therein a water wettable polymer formed by copolymerizing divinylbenzene and N-vinylpyrrolidine at a ratio of divinylbenzene to N-vinylpyrrolidine such that the poly(vinylbenzene-co-N-vinylpyrrolidone) formed is water-wettable and effective at retaining organic solutes thereon; applying to each of the wells of the multiwell plate an mixture comprising CYP2C9, tritium-labeled diclofenac labeled with tritium at the 4' position, and an analyte; contacting NADPH and optionally an NAPDH regenerating system to the mixture in each of the wells and incubating for a time sufficient for the CYP2C9 to hydroxylate the tritium-labeled diclofenac at the 4' position; optionally separating the CYP2C9 from the mixture in each of the wells of the multiwell plate; applying each mixture to a separate minicolumn of the column plate to remove the tritium-labeled diclofenac from the mixture; and, measuring amount of the tritium-labeled water in the mixture with the tritium-labeled diclofenac removed wherein a decrease in the amount of the tritium in the presence of the analyte compared to the amount of the tritium in the absence of the analyte indicates that the analyte inhibits activity of the CYP2C9.

In further aspects of the above embodiment, the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In further still aspects of any one of the above embodiments and aspects, each of the minicolumns of the column plate further comprises a porous retaining means for retaining the polymer therein. In a preferred embodiment, the wells of the multiwell plate and column plate each have a 96-well tissue culture plate format.

In a further still embodiment of any one of the above embodiments, the diclofenac labeled at the 4' position by providing a mixture of 2-iodophenyl acetic acid and 2,6-dichloro 4-bromoaniline; incubating the mixture in the presence of a copper catalyst to produce 2-[(2,6-dichloro, 4-bromophenyl)amino]phenylacetic acid; and, incubating the 2-[(2,6-dichloro, 4-bromophenyl)amino]phenylacetic acid with tritium in the presence of a palladium catalyst to produce the diclofenac labeled at the 4' position.

The present invention further provides a method for identifying an analyte that irreversibly inhibits activity of cytochrome 2C9 (CYP2C9), which comprises: providing a mixture comprising CYP2C9, NADPH regenerating system, and the analyte; incubating the mixture for different times; diluting the mixture and then adding to the diluted mixture diclofenac labeled with tritium at the 4' position and NADPH; incubating the diluted mixture for a time sufficient for the CYP2C9 to hydroxylate the tritium-labeled diclofenac at the 4' position; removing the CYP2C9 from the mixture; applying the mixture to a sorbent which preferentially binds non-polar compounds to remove the tritium-labeled diclofenac from the mixture; and measuring amount of the tritium in the mixture of step (d) with the tritium-labeled diclofenac removed, wherein a decrease in the amount of the tritium indicates that the analyte irreversibly inhibits activity of the CYP2C9.

In a further aspect of the above embodiment, the sorbent comprises a water-wettable polymer formed by copolymerizing at least one hydrophilic monomer and at least one lipophilic monomer in a ratio sufficient for the polymer to be water-wettable and effective at retaining organic solutes thereon. In further aspects of the above embodiment, the lipophilic monomer comprises a phenyl, phenylene, ether, or $C_2$-$C_{18}$ alkyl group. In a further still aspect, the lipophilic monomer is divinylbenzene. In further aspects of the above embodiments, the hydrophilic monomer comprises a saturated, unsaturated, or aromatic heterocyclic group. In a further still aspect, the hydrophilic monomer is N-vinylpyrrolidone. In further still aspects of the above embodiment, the water wettable polymer is poly(vinylbenzene-co-N-vinylpyrrolidone), preferably, a polymer wherein the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone comprises from about 15 mole percent to about 30 mole percent N-vinylpyrrolidone.

In another aspect of the above embodiment, the sorbent comprises a non-polar group bonded to a silica substrate. In a further still aspect, the sorbent comprises one or more silanes selected from the group consisting phenyl silane, dimethylsilane, trimethylsilane, ethyl silane, butyl silane, hexyl silane, octyl silane, and octadecyl silane. In further still aspects, the silica substrate is selected from the group consisting of silica particles and silica gel.

In particular embodiments of any one of the above embodiments and aspects, the CYP2C9 is provided in microsomes. The microsomes can be produced from cells selected from the group consisting of mammalian and insect cells, wherein the cells include a vector (e.g., viral or plasmid vectors) expressing the CYP2C9 or the microsomes can be from kidney, liver, brain, muscle, or the like cells. Preferably, the microsomes are human liver microsomes (HLM). In particular embodiments of any one of the above embodiments and aspects which use HLM as the source for CYP2C9, the HLM are removed from the aqueous mixture by acidification and/or centrifugation.

In a further embodiment, the present invention provides a method for determining the activity of CYP2C9 in hepatocytes, which comprises providing a culture of the hepatocytes; incubating the hepatocytes in a medium comprising diclofenac labeled with tritium at the 4' position for a time sufficient for the CYP2C9 to hydroxylate the tritium-labeled diclofenac; removing the medium from the culture of hepatocytes; applying the medium to a sorbent which preferentially binds non-polar compounds to remove the tritium-labeled diclofenac from the medium; and measuring amount of the tritium in the medium) with the tritium-labeled diclofenac removed, which determines the activity of the CYP2C9 in the hepatocytes.

In a further still embodiment, the present invention provides a method for identifying an analyte that induces CYP2C9 expression, which comprises providing a culture of hepatocytes; incubating the hepatocytes in a medium comprising the analyte; replacing the medium comprising the analyte with a second medium comprising diclofenac labeled with tritium at the 4' position and incubating the hepatocytes for a time sufficient for the CYP2C9 to hydroxylate the tritium-labeled diclofenac at the 4' position; removing the second medium from the culture of hepatocytes; applying the second medium to a sorbent, which preferentially binds non-polar compounds, to remove the tritium-labeled diclofenac from the medium; and measuring amount of the tritium in the second medium with the tritium-labeled diclofenac removed wherein an increase in the amount of tritium compared to a control culture of hepatocytes incubated with the tritium labeled diclofenac and without the analyte indicates that the analyte induces CYP2C9 expression. Preferably, the hepatocytes are incubated in the medium comprising the analyte for between about 24 to 78 hours.

In a further embodiment, the present invention provides a method for identifying an analyte that inhibits CYP2C9 activity, which comprises providing a culture of hepatocytes; incubating the hepatocytes in a medium comprising diclofenac labeled with tritium at the 4' position and the analyte for a time sufficient for the CYP2C9 to hydroxylate the tritium-labeled diclofenac; removing the medium from the culture of hepatocytes; applying the medium to a sorbent, which preferentially binds non-polar compounds, to remove the tritium-labeled diclofenac from the medium; and measuring amount of tritium in the medium with the tritium-labeled diclofenac removed wherein a decrease in the amount of tritium compared to a control culture of hepatocytes incubated with the tritium labeled diclofenac and without the analyte indicates that the analyte inhibits the CYP2C9 activity.

In a further aspect of the above embodiments, the culture of hepatocytes is provided in one or more wells of a mutiwell plate and the sorbent is provided packed in one or more solid phase extraction cartridges or columns comprising a column plate.

In a further aspect of the above embodiments, the sorbent comprises a water-wettable polymer formed by copolymerizing at least one hydrophilic monomer and at least one lipophilic monomer in a ratio sufficient for the polymer to be water-wettable and effective at retaining organic solutes thereon. In further aspects of the above embodiment, the lipophilic monomer comprises a phenyl, phenylene, ether, or $C_2$-$C_{18}$ alkyl group. In a further still aspect, the lipophilic monomer is divinylbenzene. In further aspects of the above embodiments, the hydrophilic monomer comprises a saturated, unsaturated, or aromatic heterocyclic group. In a further still aspect, the hydrophilic monomer is N-vinylpyrrolidone. In further still aspects of the above embodiment, the water wettable polymer is poly(vinylbenzene-co-N-vinylpyrrolidone), preferably, a polymer wherein the poly(vinylbenzene-co-N-vinylpyrrolidone) comprises more than 12 mole percent N-vinylpyrrolidone, more preferably, a polymer wherein the poly(vinylbenzene-co-N-vinylpyrrolidone) comprises from about 15 mole percent to about 30 mole percent N-vinylpyrrolidone.

In another aspect of the above embodiment, the sorbent comprises a non-polar group bonded to a silica substrate. In a further still aspect, the sorbent comprises one or more silanes selected from the group consisting phenyl silane, dimethylsilane, trimethylsilane, ethyl silane, butyl silane, hexyl silane, octyl silane, and octadecyl silane. In further still aspects, the silica substrate is selected from the group consisting of silica particles and silica gel.

In further aspects of the above embodiments, the diclofenac labeled at the 4' position by providing a mixture of 2-iodophenyl acetic acid and 2,6-dicloro 4-bromoaniline; incubating the mixture in the presence of a copper catalyst to produce 2-[(2,6-dichloro, 4-bromophenyl)amino]phenylacetic acid; and, incubating the 2-[(2,6-dichloro, 4-bromophenyl)amino]phenylacetic acid with tritium in the presence of a palladium catalyst to produce the diclofenac labeled at the 4' position.

The present invention further provides a method for producing diclofenac labeled at the 4' position with tritium, which comprises providing a mixture of 2-iodophenyl acetic acid and 2,6-dicloro-4-bromoaniline; incubating the mixture in the presence of a copper catalyst to produce 2-[(2,6-dichloro, 4-bromophenyl)amino]phenylacetic acid; and, incubating 2-[(2,6-dichloro, 4-bromophenyl)amino]phenylacetic acid with tritium in the presence of a palladium catalyst to produce the diclofenac labeled at the 4' position. Preferably, a tritium gas is used to produce the [4-$^3$H]-diclofenac.

The present invention further provides diclofenac labeled at the 4' position with tritium ([4-$^3$H]-diclofenac) and 2-[(2,6-dichloro, 4-bromophenyl)amino]phenylacetic acid (4'-bromodiclofenac).

As used herein, the term "analyte" refers to molecules, compounds, chemicals, compositions, drugs, and the like.

DETAILED DESCRIPTION OF THE INVENTION

Figure 1:
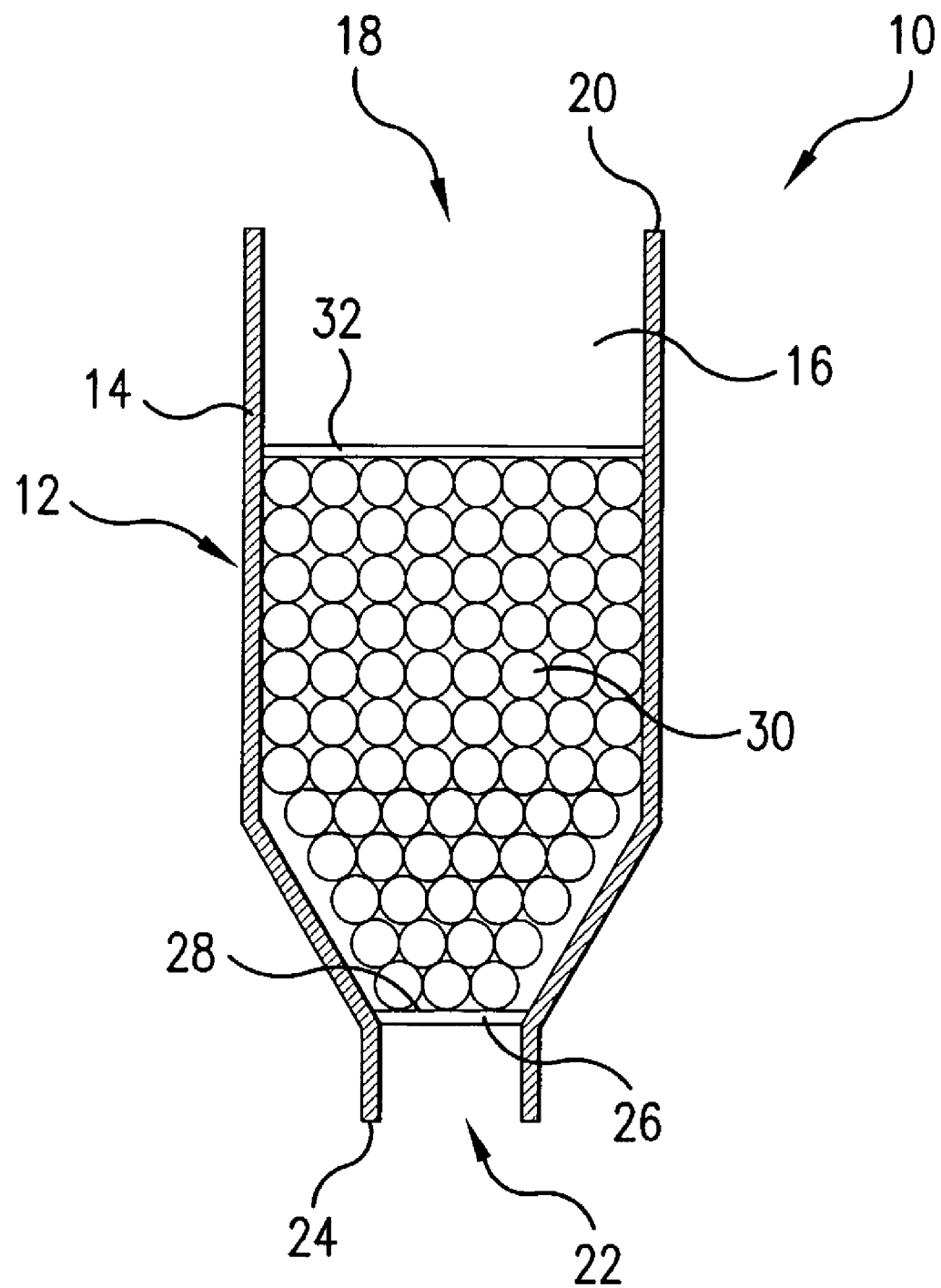
FIG. 1 shows a cross-sectional view of an extraction cartridge or column 10.

The present invention provides a rapid and sensitive diclofenac 4'-hydroxylation assay for assessing cytochrome P-450 isoform 2C9 (CYP2C9) activity and for identifying modulators of CYP2C9 activity. In particular, the present invention provides an assay for assessing the activity of CYP2C9 in mixtures comprising CYP2C9. The assays include both reversible inhibition assays and mechanism-based or time-dependent inhibition assays. Examples of such mixtures include microsomes from various tissues such as human liver microsomes (HLM); microsomes from mammalian or insect cells containing an expression vector which expresses recombinant CYP2C9; or hepatocytes, the potential of an analyte to inhibit CYP2C9 activity in any of the above mixtures, and the potential of an analyte to induce CYP2C9 expression in hepatocytes. Preferably, the CYP2C9 is a human CYP2C9. The assay is based on detecting the release of tritium as [$^3$H]—H$_2$O which occurs upon CYP2C9-mediated 4'-hydroxylation of diclofenac labeled with tritium in the 4' position in the presence of the analyte wherein an increase or decrease in release of the tritium over time indicates that the analyte is a modulator of CYP2C9 activity. For example, a decrease in the release of tritium in HLM in the presence of an analyte indicates that the analyte is an inhibitor of CYP2C9 activity whereas an increase in the release of tritium in hepatocytes after treatment of the hepatocytes with the an analyte indicates that the analyte is an inducer of CYP2C9 activity. The tritiated water product is separated from tritiated diclofenac in a solid-phase extraction process using a sorbent comprising a substrate which preferentially binds non-polar compounds such as diclofenac. All the steps of the assay, including incubations, product separation, and radioactivity counting are performed in a multiwell format, which can be automated.

The embodiment for identifying analytes that induce or inhibit CYP2C9 activity using hepatocytes in one aspect identifies analytes that inhibit or induce expression of the gene encoding CYP2C9, i.e., analytes which affect transcription of the gene encoding CYP2C9. The embodiment in another aspect identifies analytes that exert their inhibitory or inducing effect on CYP2C9 activity by affecting posttranscriptional processing of mRNA encoding the CYP2C9. The embodiment in a further aspect identifies analytes that exert their inhibitory or inducing effect on CYP2C9 activity by affecting translation of the mRNA encoding the CYP2C9. The embodiment in a further still aspect identifies analytes that exert their inhibitory or inducing effect on CYP2C9 activity by interacting directly or indirectly with the CYP2C9.

The embodiment for assessing CYP2C9 activity is useful for controlling the activity of commercial batches of hepatocytes or the quality of hepatocytes isolated in house, for instance, before using these hepatocytes to perform metabolic stability studies with new chemical entities. The embodiment for identifying CYP2C9 modulators is useful for assessing the CYP2C9 inhibition or induction potential of drug candidates in order to exclude drug candidates that are potent inhibitors or inducers from further development. In either embodiment, the present invention is an improvement over assays of the prior art which rely on HPLC separation and mass spectrometry to assess the CYP2C9 inhibition or induction potential of an analyte.

While the assays are described herein using HLM or hepatocytes, the assays can use purified recombinant CYP2C9 or microsomes prepared from other tissues, for example, kidney, intestine, lung, or the like, or other subcellular fractions containing microsomes. The microsomes can be prepared from mammalian cells containing a plasmid or viral vector that expresses CYP2C9, preferably, a human CYP2C9. The microsomes can be from insect cells infected with recombinant baculovirus expressing CYP2C9 and a p450 reductase. The advantage of the cells expressing recombinant CYP2C9 is that CYP2C9 is the only cytochrome P450 present in these microsomes and the specific activity is generally higher. The concentration range for assays using recombinant CYP2C9 is from about 1 to 100 pmol/mL, preferred concentrations are between about 5 to 50 pmol/mL. For time-dependent assays, the enzyme should be 5-10-fold higher (because of the final dilution in the second incubation).

To test an analyte for inhibition of CYP2C9 activity, a first container is provided which contains an aqueous mixture comprising the analyte to be tested for an inhibitory effect on CYP2C9 activity, diclofenac labeled with tritium at the 4' position as the substrate probe, unlabelled diclofenac to provide an adequate concentration of substrate, pooled HLM, and a buffer at a physiological pH. Typically, between about 10,000 to 1,000,000 dpm of tritium labeled diclofenac is used, preferably, the labeled diclofenac is at about 100,000 dpm. The amount of unlabelled diclofenac is between about 1 to 100 µM, typically at about 10 µM. The pooled HLM are generally at about 0.05 to 1 mg/mL, typically, about 0.1 mg/mL. An example of a suitable buffer is 0.1 M potassium phosphate, pH 7.6). The final volume is preferably between about 100 µL. Preferably, a control containing an equivalent amount of the vehicle used for the analyte is provided.

Following a preferred preincubation step of microsomes in buffer for several minutes at 37° C., about 1 mM NADPH with or without an NADPH regenerating system comprising about 5 mM glucose-6-phosphate, about 3 mM MgCl2, and about 1 unit/mL glucose-6-phosphate dehydrogenase is added to the aqueous mixture to form a reaction mixture which is then incubated at 37° C. for a period of time sufficient to allow 4' hydroxylation of the diclofenac. In a preferred embodiment, the NADPH is added with a regenerating system. In general, about 10 minutes is usually sufficient to detect CYP2C9 activity. In some cases, a multiplicity of assays are performed for various lengths of time. The reaction mixture is then stopped by addition of an acid such as HCl at a concentration of about 0.1 N. Preferably, the HLM are removed from the aqueous mixture before transferring the reaction mixture to an extraction cartridge or column for separating tritiated water from the tritiated diclofenac. The HLM can be removed from the aqueous layer by filtration, centrifugation, or the like. In a preferred embodiment, the HLM are removed by centrifugation. Because the acidification of the reaction causes the proteins in the HLM to precipitate, the proteins of the HLM can be removed using low speed centrifugation.

The aqueous mixture with the HLM removed or the reaction mixture containing the HLM is transferred to an extraction cartridge or column containing a sorbent which preferentially binds non-polar compounds such as diclofenac. The void volume or flow-through from the column is collected in a second container. The sorbent in the column is washed with water and the washes transferred to the second container. Scintillation fluid is added to the second container and the tritium released from the tritiated diclofenac by CYP2C9 is measured. Alternatively, the void volume or flow-through and washes are transferred to a scintillation vial and mixed with scintillation fluid for measuring the tritium in a scintillation counter. The absence of tritiated water or reduced amounts of tritiated water compared to the amounts of tritiated water in the positive controls indicate that the analyte is an inhibitor of CYP2C9 activity.

The CYP2C9 activity of a preparation of hepatocytes is determined as follows. Primary cultures of hepatocytes, which can comprise hepatocytes freshly isolated from liver tissue or which had been isolated previously, frozen for storage, and thawed for the assay, are provided. The hepatocytes are maintained at 37° C. in a humidified atmosphere of 5% $CO_2$ and 95% air or oxygen in a culture medium or aqueous mixture suitable for culturing hepatocytes (See for example, Dich and Grunnet in Methods in Molecular Biology, Vol. 5: Animal Cell Culture (Pollard and Walker, eds) pp. 161-176, Humana Press, Clifton, N.J. (1989). The assay can be performed using either cells in suspension or cultured cells attached to cell culture plates. For suspension assays, typically, the hepatocytes are incubated at a concentration of about $1\times10^5$ cells/mL to $1\times10^6$ cells/mL, preferably $1\times10^6$ cells/mL. Thus, each culture well contains about $1\times10^6$ cells, 1 mL of hepatocyte culture medium (HCM) (Dich and Grunnet, ibid.), unlabelled diclofenac, and tritium-labeled diclofenac. Typically, between about 100,000 to 2,000,000 dpm of tritium labeled diclofenac is used. The amount of unlabelled diclofenac is preferably between about 1 to 50 µM, typically at about 10 µM. For assays in plated cells, the hepatocytes are plated onto tissue culture plates (preferably, the culture plates are collagen-coated 24- or 96-well tissue culture plates) and maintained at 37° C. in a humidified atmosphere of 5% $CO_2$ in a culture medium suitable for culturing fresh hepatocytes, e.g., HCM. Preferably, the medium is supplemented with ITS. Typically, the hepatocytes are plated at a density of about 150,000 to 200,000 cells/cm².

Following the incubation, the incubation medium is removed from the cells, for instance by centrifugation, and transferred to an extraction cartridge or column containing a sorbent which preferentially binds non-polar compounds such as diclofenac. The void volume or flow-through from the column is collected in a second container. The sorbent in the column is washed several times with water and the washes transferred to the second container. Scintillation fluid is added to the second container and the tritium released from the tritiated diclofenac by CYP2C9 is measured. Alternatively, the void volume or flow-through and washes are transferred to a scintillation vial and mixed with scintillation fluid for measuring the tritium in a scintillation counter. The amounts of tritiated water produced determines the relative CYP2C9 activity of the hepatocytes.

The assay for determining the ability of an analyte to inhibit CYP2C9 activity is as follows. Primary cultures of hepatocytes, which can comprise hepatocytes freshly isolated from liver tissue or which had been isolated previously, frozen for storage, and thawed for the assay, are provided. The assay can be performed using either cells in suspension or cultured cells attached to cell culture plates. For suspension assays, the hepatocytes are maintained at 37° C. in a humidified atmosphere of 5% $CO_2$ in a culture medium suitable for culturing hepatocytes as above. Typically, the hepatocytes are incubated at a concentration of about $1\times10^6$ cells/mL. For non-suspension assays, the hepatocytes are plated to tissue culture plates (preferably. Collagen coated tissue culture plates) and maintained at 37° C. in a humidified atmosphere of 5% $CO_2$ in a culture medium suitable for culturing hepatocytes, e.g., HCM. Thus, each culture well contains about $1 \times 10^6$ cells, 1 mL of HCM, the analyte being tested for inhibitory effect on CYP2C9 activity, unlabelled diclofenac, and tritium-labeled diclofenac. Typically, between about 100,000 to 2,000,000 dpm of tritium labeled diclofenac is used, preferably, about 500,000 dpm/mL. The amount of unlabelled diclofenac is between about 1 to 50 μM, typically at about 10 μM. Preferably, controls that include the vehicle for the analyte or a CYP2C9 inhibitor such as sulfaphenazole are provided.

Following the incubation, the incubation medium is removed from the cells and transferred to an extraction cartridge or column containing a sorbent which preferentially binds non-polar compounds such as diclofenac. The void volume or flow-through from the column is collected in a second container. The sorbent in the column is washed several times with water and the washes transferred to the second container. Scintillation fluid is added to the second container and the tritium released from the tritiated diclofenac by CYP2C9 is measured. Alternatively, the void volume or flow-through and washes are transferred to a scintillation vial and mixed with scintillation fluid for measuring the tritium in a scintillation counter. The absence of tritiated water or reduced amounts of tritiated water compared to the amounts of tritiated water in the control comprising the vehicle only indicates that the analyte is an inhibitor of CYP2C9 activity.

The assay for determining the ability of an analyte to induce CYP2C9 activity is as follows. Primary cultures of hepatocytes, which can comprise hepatocytes freshly isolated from liver tissue or which had been isolated previously, frozen for storage, and thawed for the assay, are provided. The hepatocytes are plated onto tissue culture plates (preferably, the culture plates are collagen-coated 24- or 96-well tissue culture plates) and maintained at 37° C. in a humidified atmosphere of 5% $CO_2$ in a culture medium suitable for culturing fresh hepatocytes, e.g., HCM. Preferably, the medium is supplemented with ITS. Typically, the hepatocytes are plated at a density of about 150,000 to 200,000 cells/$cm^2$. Twenty-four to 78 hours later, the culture medium is removed and fresh medium and the analyte to be tested for induction potential are added to the hepatocytes. Preferably, controls are provided which comprise either the vehicle for the analyte or a known inducer such as rifampicin or phenobarbitol or the like. After incubating the hepatocytes as above for time sufficient for induction of CYP2C9, usually between about 24 to 78 hours is sufficient, CYP2C9 enzyme activity is determined.

The hepatocytes are incubated in an incubation medium containing a balanced salt solution containing a buffer at physiological pH, for example, pH 7.4. An example of a balanced salt solution is Hank's balanced salt solution and an example of a suitable buffer is 10 mM HEPES. Then a mixture containing unlabelled diclofenac and tritium-labeled diclofenac is added and the hepatocytes incubated as above for a suitable time to assess CYP2C9 activity, about an hour is usually sufficient. Typically, between about 100,000 to 2,000,000 dpm/mL of tritium labeled diclofenac is used, preferably, the labeled diclofenac is at about 500,000 dpm/mL. The amount of unlabelled diclofenac is between about 1 to 50 μM, typically at about 10 μM. Optionally, parallel incubations are performed, which contain the CYP2C9 inhibitor sulfaphenazole, to ascertain that detected enzyme activity is specifically mediated by CYP2C9.

Following the incubation, the incubation medium is removed from the cells and transferred to an extraction cartridge or column containing a sorbent which preferentially binds non-polar compounds such as diclofenac. The void volume or flow-through from the column is collected in a second container. The sorbent in the column is washed with water and the washes transferred to the second container. Scintillation fluid is added to the second container and the tritium released from the tritiated diclofenac by CYP2C9 is measured. Alternatively, the void volume or flow-through and washes are transferred to a scintillation vial and mixed with scintillation fluid for measuring the tritium in a scintillation counter. The presence of tritiated water or increased amounts of tritiated water compared to the amounts of tritiated water in the control with the vehicle only indicates that the analyte is an inducer of CYP2C9 activity.

As discussed below and shown in Example 1, in a preferred aspect of the present assay, the assay is performed in a multiwell format, preferably, a 96-well format. The multiwell format enables a plurality of analytes to be tested simultaneously. In the multiwell format, each reaction is conducted in the well of a multiwell plate (first container). The separation of tritiated water from tritiated diclofenac at the conclusion of the reaction and following the optional step of removing the HLM is performed by applying each reaction to a separate column of a microfiltration/extraction column plate comprising a plurality of miniature columns, each containing the sorbent disclosed herein. Preferably, the columns of the microfiltration/extraction column plate are arranged in the same format as the format for the multiwell plate. The void volume and washes are collected in a second multiwell plate in the same format as the microfiltration/extraction column plate, mixed with scintillation fluid, and counted in a scintillation counter adapted for counting samples in a multiwell format.

The sorbent preferentially binds non-polar compounds such as diclofenac, i.e., the sorbent can adsorb or bind the labeled diclofenac but not the labeled water produced by the hydroxylation. Sorbents which preferentially bind non-polar compounds such as diclofenac include, but are not limited to, sorbents comprising a hydrophobic or lipophilic polymer such as polystrene-divinylbenzene or poly(divinyl-benzene-vinylpyrrolidone), water-wettable polymers comprising lipophilic and hydrophilic monomers in a ratio that enables the sorbent to bind the labeled diclofenac but not tritiated water, and silicon-based sorbents such as the $C_2$-$C_{18}$ silanes.

The sorbent comprising a water-wettable polymer is formed by copolymerizing at least one hydrophilic monomer and at least one lipophilic monomer in a ratio sufficient for the polymer to be water-wettable and effective at retaining organic solutes thereon. The lipophilic monomer can comprise a lipophilic moiety such as phenyl, phenylene, and $C_2$-$C_{18}$-alkyl groups. Particularly useful lipophilic monomers include divinylbenzene and styrene. The hydrophilic monomer can comprise a hydrophilic moiety such as a saturated, unsaturated, or aromatic heterocyclic groups, for example, a pyrrolidonyl group or a pyridyl group. Alternatively, the hydrophilic group can be an ether group. Particularly useful monomers include N-vinylpyrrolidone, 2-vinylpyridine, 3-vinylpyridine, 4-vinylpyridine, and ethylene oxide. In one embodiment of the water-wettable polymer, the polymer is a poly(divinylbenzene-co-N-vinylpyrrolidone) copolymer comprising greater than about 12 mole percent N-vinylpyrrolidone, preferably, from about 15 mole percent to about 30 mole percent N-vinylpyrrolidone. Examples of preferred water wettable polymers are disclosed in WO9738774 and U.S. Pat. No. 6,726,842, both to Bouvier et al. An example of the preferred sorbent is the OASIS HLB sorbent, which comprises a balanced ratio of N-vinylpyrrolidone and divinylbenzene monomers, and is commercially available from Waters Corporation (Newcastle, Del.).

Sorbents comprising a silicon-based substrate or matrix include a non-polar group bonded to a silica substrate. The sorbent can comprise one or more silanes well known in the art for extracting non-polar compounds. Such sorbents include, but are not limited to, phenyl silane, butyldimethyl silane, dimethylsilane, trimethylsilane, ethyl silane, butyl silane, hexyl silane, octyl silane, or octadecyl silane. The silanes can be monofunctional or trifunctional. The silica substrate or matrix includes, but is not limited to, solid or porous silica or ceramic particles or microparticles or silica gel.

In a preferred embodiment of the method, the sorbent is provided as particles, beads, or the like of the sorbent which are packed within an open-ended container to form a solid phase extraction cartridge or column. In particular embodiments of the method, the sorbent is packed into the solid phase extraction cartridge or column enmeshed in a porous membrane. In other embodiments, the solid phase extraction cartridge or column further includes a porous retaining means, such as a filter element, or frit at or near one or both ends of the solid phase extraction cartridge or column adjacent to the sorbent. The porous retaining means is to retain the sorbent within the solid phase extraction cartridge or column. In a further embodiment, the sorbent is disposed between a pair of porous retaining means, the first porous retaining means to retain the sorbent within the solid phase extraction cartridge or column and the second retaining means also aids in retaining the sorbent within the column and to prevent solid materials such as HLM from mixing with the sorbent. The filter or frit can be, for example, fritted glass, or a porous polymer such as high density polyethylene, TEFLON (E.I du Pont de Nemours and Company, DE), or polycarbonate.

FIG. 1 shows a cross-sectional view of an example of a solid phase extraction cartridge or column 10 which is suitable for practicing the method of the present invention. The column 10 comprises an elongated body 12 having wall 14, which defines an axial hollow portion 16, an inlet 18 at the distal end 20 of the column 10 for receiving an aqueous mixture, and outlet 22 at the proximal end 24 of the column 10 for exit of the aqueous mixture. As further shown in FIG. 1, adjacent to the proximal end 24 is a porous retaining means 26 which has surface 28. The porous retaining means 26 is positioned adjacent to the proximal end 24 in column 10 so that surface 28 is perpendicular to wall 14 of column 10. Disposed on surface 28 of the porous retaining means 26 is sorbent 30. Optionally, as shown, a second porous retaining means 32 can be positioned adjacent to or near the distal end 20 and the sorbent 30 disposed therebetween. The column 10 enables the aqueous mixture to enter the container through the inlet 18, contact the sorbent 30 within the column 10, and exit the column 10 through the outlet 22. Preferably, the sorbent 30 is packed in the column 10 as small particles such as beads having a diameter preferably between about 30 to 60 μm.

Figure 2:
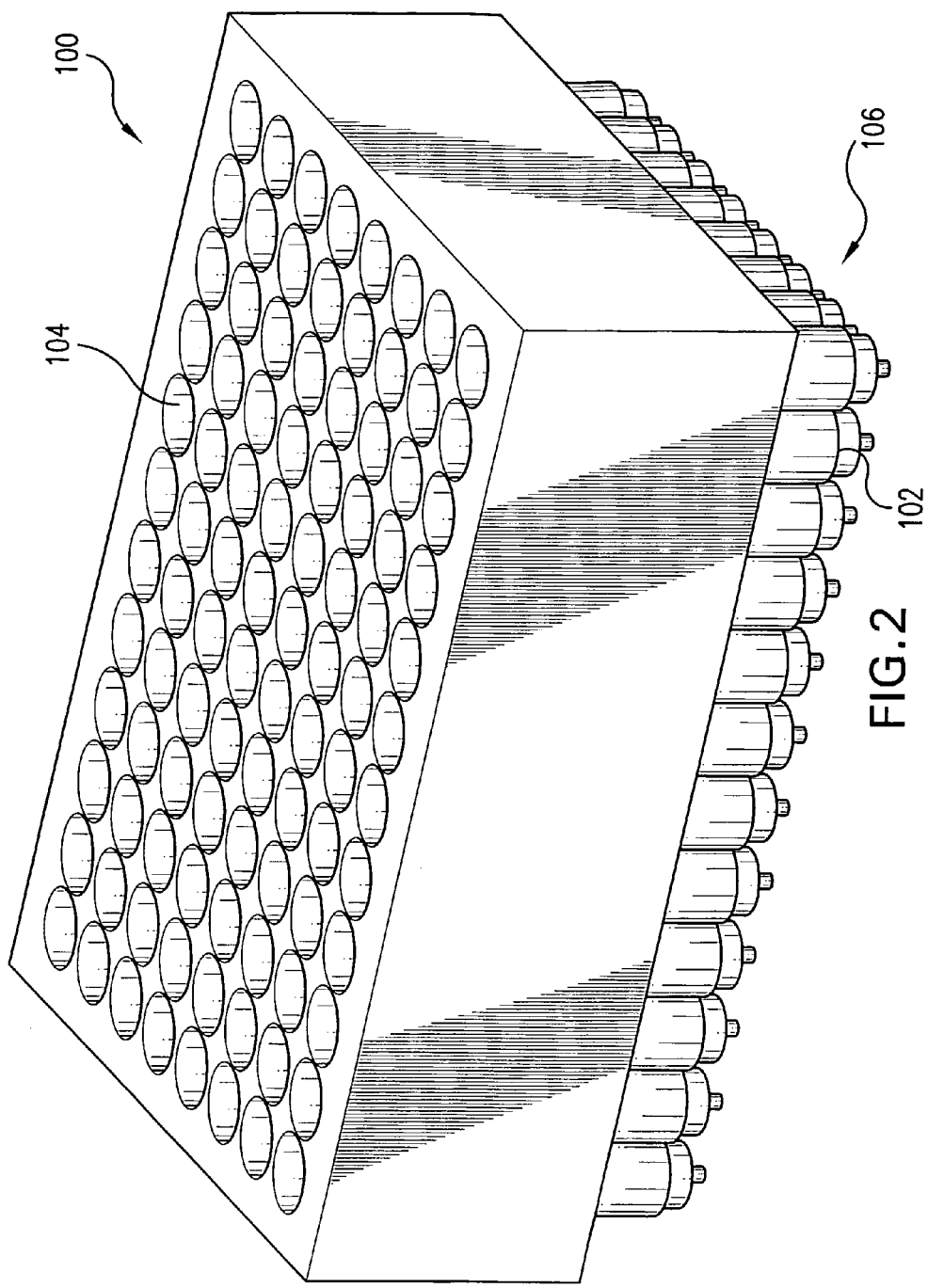
FIG. 2 shows a perspective view of a multicolumn microfiltration/extraction plate 100.

In a preferred embodiment, a multiplicity of the columns 10 are arranged to provide a format which is particularly suitable for high throughput screening. For example, a multicolumn microfiltration/extraction column plate comprising a multiplicity of wells adapted to provide solid phase extraction cartridges or columns (preferably, miniature solid phase extraction cartridges or columns, i.e., minicolumns). A preferred multicolumn microfiltration/extraction column plate format has the minicolumns arranged in a format that corresponds to the format used for multiwell tissue culture plates. For example, the minicolumns of the microfiltration/extraction column plate can be arranged in a 6-well, 12-well, 24-well, 48-well, 96-well, or 384-well format. In a preferred embodiment, the multicolumn microfiltration/extraction column plate has the minicolumns arranged in a 96-well format. As an example, FIG. 2 shows a multicolumn microfiltration/extraction plate 100 comprising a multiplicity of minicolumns 102 with opening 104 for receiving an aqueous mixture and outlet 106 for exit of the aqueous mixture wherein each of the minicolumns 102 comprises an internal arrangement similar to that shown for column 10 of FIG. 2 arrayed in a 96-minicolumn format. Movement of the aqueous mixture through the column and into a collecting plate containing wells arranged in a 96-well format can be achieved by centrifugation or by vacuum. Multi-column microfiltration/extraction column plates and methods and apparatus for using the plates have been disclosed in a number of U.S. Patents, for example, U.S. Pat. No. 6,506,343 to Bodner et al., U.S. Pat. No. 6,491,873 to Roberts and Woelk, and U.S. Pat. No. 6,338,802 to Bodner et al., and U.S. Published Patent Application No. 20030143124 to Roberts and Grenz.

In addition to reversible inhibition of CYP, irreversible or quasi-irreversible inactivation by certain analytes or their CYP-generated metabolites can occur. This type of inhibition, termed mechanism-based or time-dependent inhibition (MBI), is characterized by a progressive time-dependent decrease in enzyme activity in the presence of inhibitor. Three types of mechanism-based (time-dependent) inactivation of CYP have been reported: (i) inhibitor covalently binds to enzyme apoprotein; (ii) inhibitor covalently binds to prosthetic heme; (iii) inhibitor tightly (quasi-irreversibly) binds to heme or apoprotein. Most human hepatic drug-metabolizing CYPs, including CYP3A4/5, CYP2C9, CYP1A2, CYP2D6, CYP2C19, CYP2A6, CYP2B6 and CYP2E1 are subject to mechanism-based inhibition (MBI) (Zhang and Wong, Curr. Drug Metab. 6: 241-257 (2005); Venkatakrishnan et al., Curr. Drug Metab. 4: 423-459 (2003); Zhou et al., Curr. Drug Metab. 5: 415-442 (2004); Zhou et al., Clin. Pharmacokinet. 44: 279-304 (2005)).

In contrast to reversible CYP inhibition, whose effects are not always manifest in vivo, MBI almost invariably leads to clinically relevant drug-drug interactions. Indeed, it is currently thought that MBI might be one of the major causes for clinical drug-drug interactions, which has been potentially overlooked in the past.

Since MBI leads to a time-dependent loss of active enzyme, the clinical effects of a time-dependent CYP inhibitor on the pharmacokinetics of a drug that is metabolized by the same CYP is as follows:

MBI causes non-stationary PK upon multiple dosing

The extent of drug-drug interaction is time-dependent in onset and offset

High concentrations of inhibitor in intestinal lumen will cause significant effects on substrates whose oral bioavailability is limited by intestinal metabolism.

Therefore, the present invention also provides mechanism-based or time-dependent assays in addition to the reversible or quasi-reversible assays described above. To assess the potential of a compound to act as a time-dependent CYP inhibitor, the analyte is preincubated with CYP2C9 in the presence of an NADPH regenerating system for a series of different lengths of time (typically from 0 minutes to 60 minutes). In general, CYP2C9 is provided at an amount about 5 to 10 times greater than the amount used in the reversible inhibition assays. Control incubations are performed in the absence of inhibitor to monitor for losses in enzyme activity due to thermal instability. At the end of the preincubation, the change in the amount of enzymatically active CYP relative to the time 0 preincubation time control is determined. This is achieved by performing a second incubation in which the preincubation is diluted and substrate is added. Enzyme activity is determined by measuring the amount of product formed during a specified time interval. Typical substrates used for time-dependent CYP inhibition assays are the same as those used for reversible inhibition assays above. For example, the $K_m$ for CYP2C9 for diclofenac is about 6 µM and the preferred concentration of diclofenac is between about 30 to 100 µM. Example 6 provides an example of a time dependent assay using HLM.

In order to minimize any reversible CYP inhibition effect caused by the test analyte in the second incubation, the preincubation mixture is diluted several-fold (typically 5-20 times), the CYP substrate is added at a concentration several times (typically 5-10 times) higher than the concentration required for half-maximal activity (to minimize competitive inhibition by test compound), and the incubation time is short (typically 10 min). If an analyte acts as a time-dependent inhibitor, preincubation with CYP will cause a loss of enzyme activity with pseudo-first order kinetics. For each inhibitor concentration, the percentage of remaining enzyme activity (relative to a control without inhibitor) will change with time according to the equation:

$$\% \text{ of remaining enzyme activity} = 100 \times e^{(-k \times t)} \qquad \text{equation 1}$$

where k is the observed pseudo-first order inactivation rate constant, which is related to the inhibitor concentration during preincubation according to the following relationship:

$$k = \frac{k_{inact} \times I^n}{K_{0.5}^n + I^n} \qquad \text{equation 2}$$

where I is the inhibitor concentration, $k_{inact}$ is the maximal inactivation rate constant, $K_{0.5}$ is the inhibitor concentration at 50% $k_{inact}$, and n is the Hill coefficient. To determine $k_{inact}$ and $K_{0.5}$, the curve of k versus I is fitted to equation 2 using non-linear regression analysis.

As shown in Example 1, the present invention also provides diclofenac labeled at the 4' position with tritium ([4'-³H]-diclofenac) and a method for making the [4'-³H]-diclofenac. The present invention further provides 2-[(2,6-dichloro, 4-bromophenyl)amino]phenylacetic acid (4'-bromodiclofenac), an intermediate to making the [4'-³H]-diclofenac, and a method for making the 4'bromodiclofenac.

The synthesis of diclofenac using the Ullman reaction has been described (Moser et al., J. Med. Chem. 33: 2358-2364, (1990); Satoh et al., J. Med Chem. 36: 3580-3594 (1993); Oza et al., J. Med Chem. 45, 321-332, (2002) and references therein). To make diclofenac labeled at the 4' position with tritium ([4'-3H]-diclofenac), the Ullman reaction was modified to produce 2-[(2,6-Dichloro, 4-bromophenyl)amino] phenylacetic acid (4'-bromodiclofenac (1)), which in the presence of tritium and a palladium catalyst was then converted to diclofenac labeled in the 4' position.

In general, the synthesis of [4'-³H]-diclofenac is by the process shown in Scheme 1. A mixture of 2-iodophenyl acetic acid and 2,6-dichloro, 4-bromoaniline is incubated in the presence of an activated copper catalyst to produce 4'-bromodifenac (1). The 4'-bromodiclofenac (1) is then incubated with tritium in the presence of a palladium catalyst to produce [4'-³H]-diclofenac.

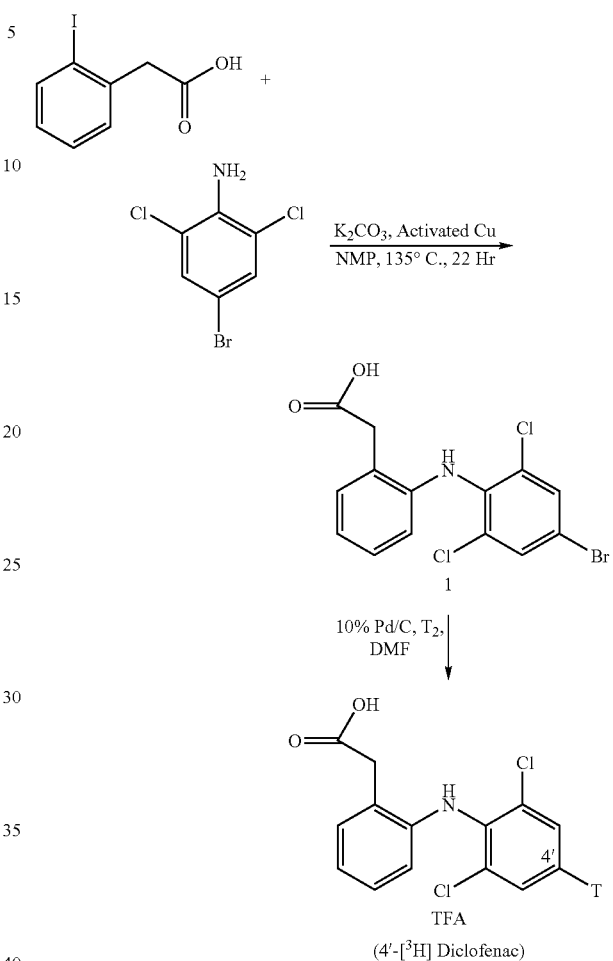

Scheme 1

The reaction for making the 4'-bromodiclofenac is preferably performed in an organic solvent such as N-methylpyrrolidone (NMP). The mixture is incubated at an elevated temperature, preferably, at a temperature of about 135° C., for a time sufficient to make the 4'-bromodiclofenac, which is when the color of the mixture turns a brown-black, in general, about 20 hours. The 4'-bromodiclofenac is preferably separated from the reactants and solvent by a chromatographic method.

The 4'-bromodiclofenac separated from the other reactants is then incubated with tritium gas and a palladium catalyst in an organic solvent such as N,N-dimethylformamide (DMF). In a preferred embodiment, the palladium catalyst is a palladium on carbon catalyst (Pd/C), preferably, wherein the percentage palladium is about 10%. In preferred embodiments, the tritium is provided as a $T_2$ gas. After time sufficient to label the diclofenac at the 4' position with tritium, usually about an hour, exchangeable tritium is removed and the [4'-³H]-diclofenac separated from other components of the reaction, preferably by a chromatographic method.

The following example is intended to promote a further understanding of the present invention.

EXAMPLE 1

The synthesis of diclofenac labeled at the 4' position with tritium as shown in Scheme 1 was as follows.

Synthesis of 4'-bromodicofenac (1) was as follows. 2-Iodophenyl acetic acid (21.3 mg, 0.08 mmol) was added to a mixture of 2,6-dichloro, 4-bromoaniline (78 mg, 0.32 mmol), anhydrous potassium carbonate (33.6 mg, 0.24 mmol), and activated copper powder catalyst (2.25 mg, 0.035 mmol) in N-methylpyrrolidone (0.5 mL). The reaction mixture was heated at 135° C. for 22 hours with stirring while water was distilled off through a descending condenser. The color of the reaction mixture changed to brown-black. The hot reaction mixture was treated with hot water and filtered through CELITE (available from World Minerals, N.J.). The crude product containing 4'-bromodiclofenac (1) was purified by using reserve phase HPLC (LUNA Phenyl Hexyl 250×10 mm column (available from Phenomenex, Torrance, Calif.), water containing 0.1% TFA:acetonitrile 50:50, flow rate 4 mL/min, UV=254 nm, Rt=23-24 min). The required fractions were collected and passed through Sep-Pak C-18 (Waters, Corp., Milford, Mass.), followed by eluting with 10 mL ethanol to yield 5 mg of 2-[(2,6-Dichloro-4-bromophenyl)amino]phenylacetic acid (1).

Synthesis of [4'-3H]-diclofenac from 4'-bromodiclofenac (1) was as follows. 4'-bromodiclofenac (1), (5 mg) was stirred with tritium gas ($T_2$ or $^3H_2$) using catalyst 10% Pd/C (5 mg) in DMF (1 mL) for one hour. The reaction mixture was filtered and co-evaporated with ethanol (2×10 mL) in order to remove any exchangeable tritium. The crude product was purified by using semi-preparative HPLC column (Luna Phenyl Hexyl, 250×10 mm column), water containing 0.1% TFA: acetonitrile 55:45, flow rate 4 mL/min, UV=254 nm, Rt=20-21 min) to yield [4'-$^3$H]-diclofenac (10 mCi, SA=22.7 Ci/mmol, as determined by LC/MS). LC/MS: 296 (M)$^+$, 298 (M+2)$^+$

EXAMPLE 2

This example illustrates the development of the assay of the present invention and its use to identify inhibitors of CYP2C9 activity.

Radiometric CYP2C9 assays using [4'-$^3$H]-diclofenac. Reactions were carried out in 96-well conical microtiter plates (available from Coming, Acton, Mass.) containing labeled diclofenac tracer (from 10,000 to 1,000,000 dpm, typically 100,000 dpm) prepared as in Example 1 and used without further purification, unlabelled diclofenac (10 µM, except otherwise noted), pooled human liver microsomes (HLM) (0.1 to 1 mg/mL, preferably 0.125 mg/ml), and 0.1 M potassium phosphate buffer, pH 7.6, in a final volume of 100 µL. Pooled HLM were obtained from Gentest Corp. (Woburn, Mass.). Inhibitors were added to the reaction mixture from stock solutions in DMSO/acetonitrile/water (35:25:40, v/v), giving final solvent concentrations of 0.7% DMSO and 0.5% acetonitrile. No inhibitor controls contained an equivalent amount of vehicle. Following preincubation for 10 minutes at 37° C., reactions were started by addition of 1 mM NADPH and an NADPH regenerating system containing 5 mM glucose-6-phosphate, 3 mM MgCl2, and 1 U/mL glucose-6-phosphate dehydrogenase. Assays were conducted for 10 minutes at 37° C. and stopped by addition of HCl to a final concentration of 0.1 N. Plates were then centrifuged for 10 minutes in a microplate rotor and supernatants loaded into the wells of a preconditioned 10 mg OASIS 96-well HLB plate. OASIS HLB 96 well extraction plates and vacuum manifold are available from Waters Corp., Newcastle, Del. Vacuum was applied and the void volume collected in the collection plate. Then, 75 µL of water was added, vacuum was applied again, and the wash was collected into the same plate. Pooled void volume and water wash were transferred into scintillation vials and counted in a beta-scintillation counter. Alternatively, aliquots were counted in 24- or 96-well scintillation plates using a TOPCOUNT scintillation counter (Packard, Perkin Elmer, Boston, Mass.). For the calculation of enzyme activity, product counts were corrected by subtraction of counts obtained in control incubations performed in the absence of NADPH regenerating system.

Quantification of 4'hydroxydiclofenac. Aliquots of the assay reaction mixture and of metabolite standard curves were analyzed by HPLC using an Agilent HP1100 liquid chromatograph (Agilent Technologies) equipped with a CTC Analytics PAL Autosampler (HTS PAL; CTC Analytics AG, Switzerland). Chromatography was performed on a XTERRA MS $C_{18}$ column (4.6 mm×5 cm; 5 µm; Waters Corp., Medford, Mass.) at a flow rate of 2 mL/min, using a mobile phase consisting of a mixture of 0.1% formic acid in water (A) and 0.1% formic acid in acetonitrile (B) (linear gradient 0 to 0.5 min, 10% B; 3.0 min 90% B, 3.5 min 90% B, 3.6 min 10% B; the system was equilibrated for 1.4 minutes at 10% B prior to the next injection). The eluate was diverted to waste for the first minute, and then to a Sciex API-3000 triple quadruple mass spectrometer (available, for example, from Perkin Elmer, Boston, Mass.) with a Turbo Ionspray ionization source operated in the positive ion mode. 4'hydroxydiclofenac was detected and identified using the transition m/z 312.1→230.0. Metabolite concentrations were determined by weighted linear least-squares regression analysis, using Analyst Quantitation Wizard software version 1.2 (Applied Biosystems, Foster City, Calif.).

Curve fitting. Curve fitting to the Hill equation or to a four-parameter logistic inhibition model (Rodbard and Frazier, Meth. Enzymol. 37: 3-22 (1975)) was performed by nonlinear regression using XLFIT 4.0 (ID Business Solutions, Inc., Guildford, UK; Emeryville, Calif.).

Results

Separation of [4'-$^3$H]-diclofenac and [$^3$H]—H$_2$O using 96-well solid phase extraction plates. When a solution of assay buffer containing labeled diclofenac (from $10^4$ to $10^7$ dpm) and stopping solution was applied to 96-well extraction plates containing 10 mg OASIS sorbent, over 99.8% of the radioactivity was retained on the plate. The labeled diclofenac could be recovered by eluting with methanol. In contrast to the labeled diclofenac, [$^3$H]—H$_2$O (from $10^2$ to $10^5$ dpm) was not retained under the same conditions. With both the 10 mg and 30 mg plates, recovery of [$^3$H]—H$_2$O eluted in the combined void volume following a 100 µL or 400 µL aqueous wash, was quantitative (94±6%, average ±SD, n=6).

Figure 3:
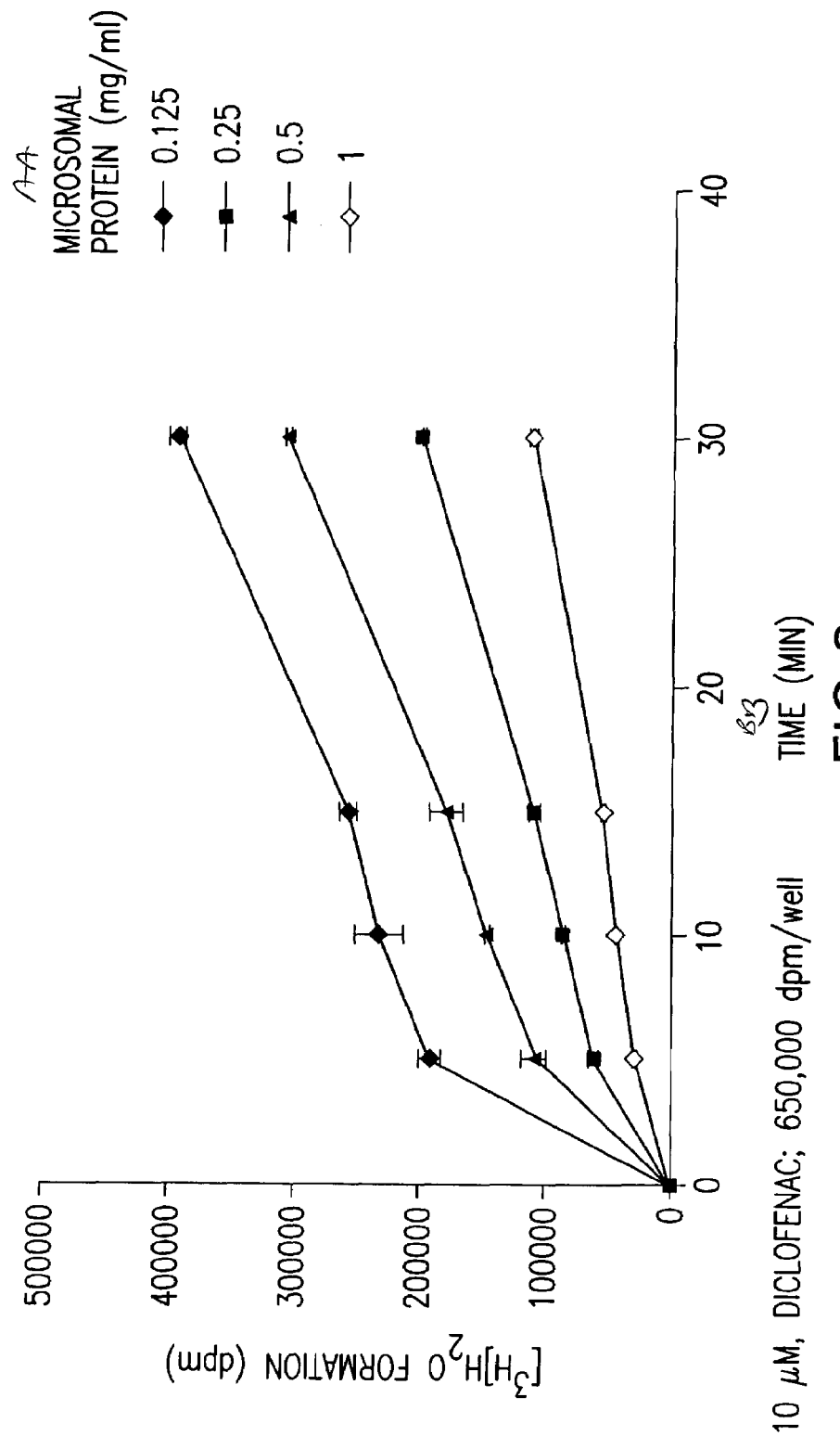
FIG. 3 shows the effect of incubation time and microsomal protein concentration on NADPH-dependent formation of tritiated water from [4'-$^3$H]-diclofenac in HLM. The assay used 10 μM diclofenac and 650,000 dpm of labeled diclofenac per well. HLM concentrations were 0.125 mg/mL, 0.25 mg/mL, 0.5 mg/mL, and 1 mg/mL.
Figure 4:
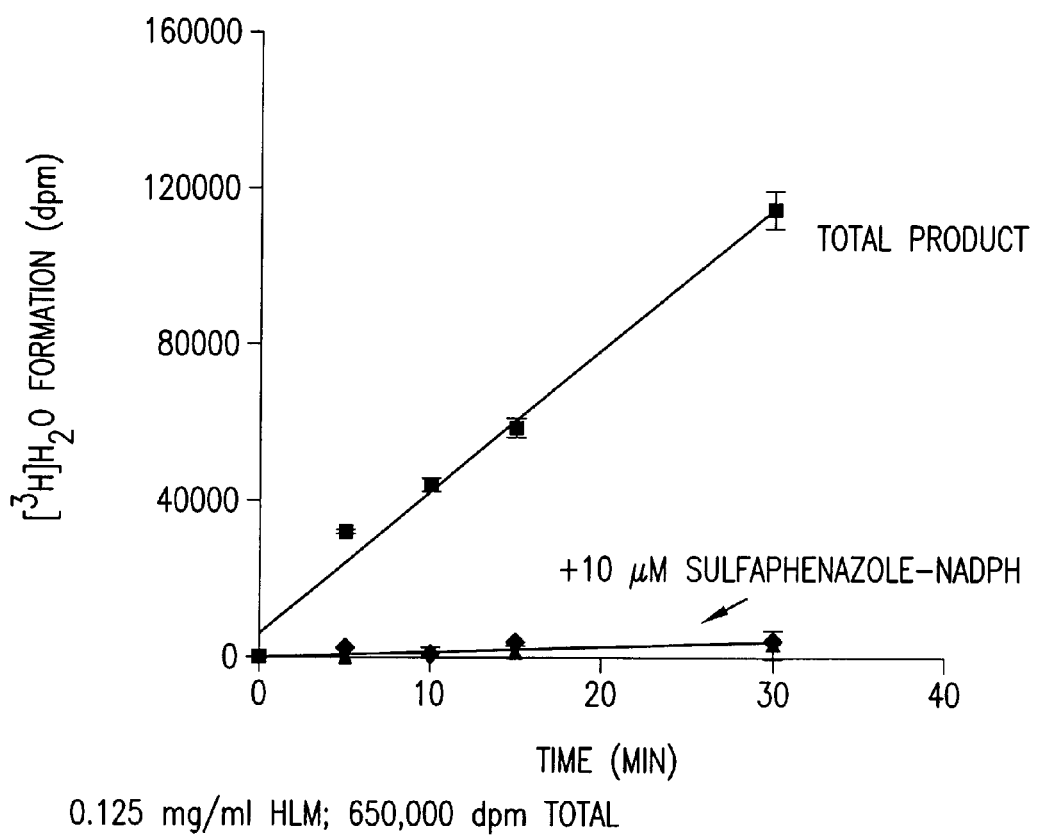
FIG. 4 shows the effect of NADPH and sulfaphenazole on the formation of tritiated water from [4'-$^3$H]-diclofenac in HLM. The assay used 10 μM diclofenac and 650,000 dpm of labeled diclofenac per well. HLM concentration was 0.125 mg/mL.

Formation of [$^3$H]—H$_2$O from [4'-$^3$H]-diclofenac in HLM. When [4'-$^3$H]-diclofenac was incubated with HLM in the presence of an NADPH regenerating system, [3H]—H$_2$O was formed in a time-dependent manner. Product formation increased linearly with the concentration of microsomes up to a protein concentration of 1.0 mg/mL (See FIG. 3). Formation of tritiated water was dependent on NADPH, indicating that the reaction was mediated by cytochrome P450. The specific CYP2C9 inhibitor sulfaphenazole inhibited NAPH-dependent formation of [$^3$H]—H$_2$O, indicating that the reaction was mediated primarily by CYP2C9 (See FIG. 4). Signal to noise ratio is defined as the ratio between product counts obtained in the presence vs. absence of NADPH. The fractional conversion rate is expressed as percent of total radiolabelled substrate converted into tritiated water per unit time and per mg of microsomal protein. Signal to noise ratios were between 30 and 50 when assays were performed for 10 minutes using 0.125 or 0.25 mg/mL of HLM. Fractional conversion rates were about 50 to 80%/min/mg.

Figure 5:
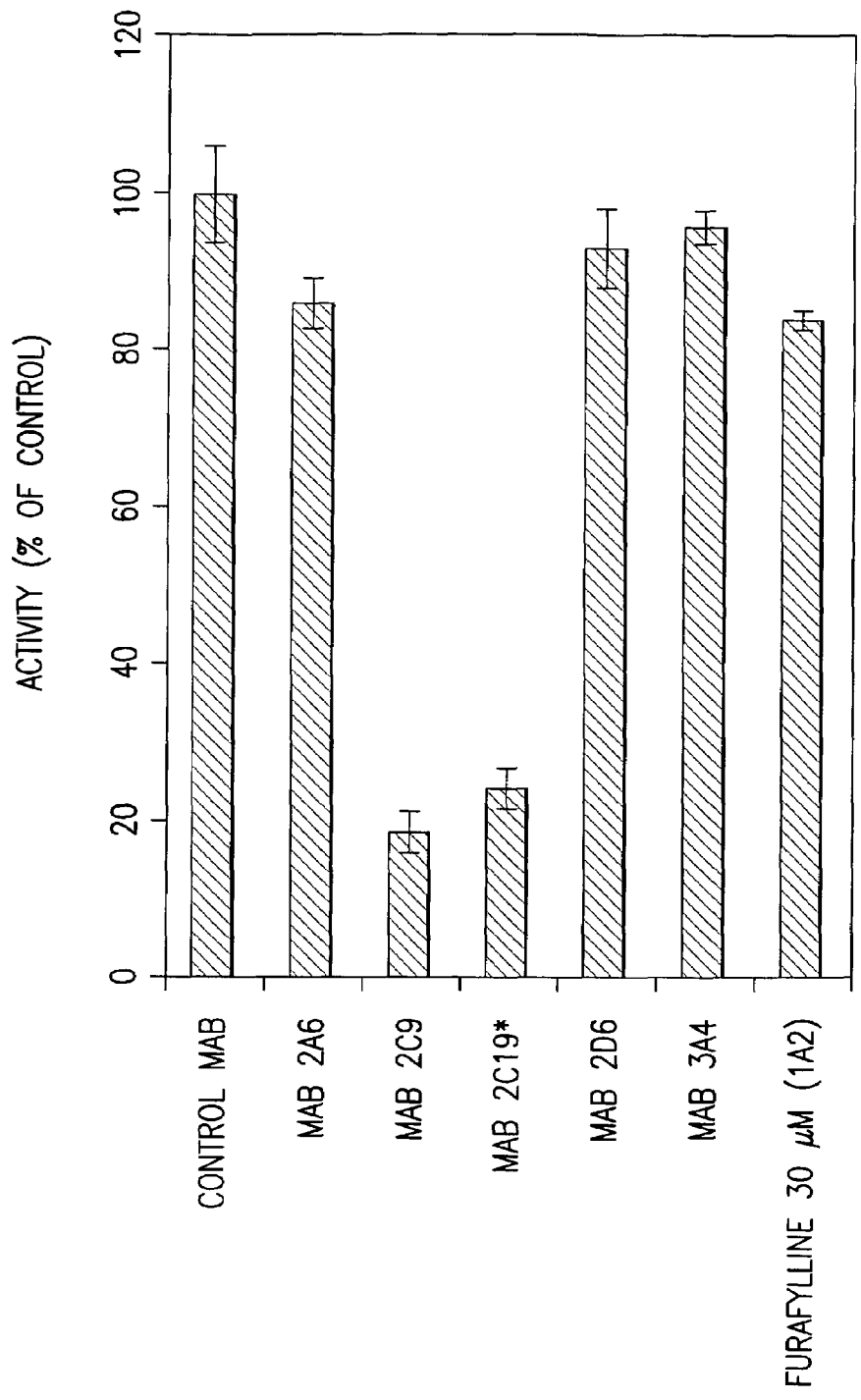
FIG. 5 shows the effect of various CYP inhibitors on NADPH-dependent formation of tritiated water from [4'-$^3$H]-diclofenac in HLM.

Effect of CYP inhibitors and anti-CYP antibodies. To confirm that CYP2C9 mediates product formation, reactions were performed in the presence or absence of a series of isoform-selective chemical inhibitors (Bourrie et al., J. Pharmacol. Exp. Ther. 277: 321-32 (1996); Eagling et al., Br. J. Clin. Pharmacol. 45: 107-14 (1998)) or monoclonal antibodies (Mei et al., J. Pharmacol. Exp. Ther. 291: 749-59 (1999); Shou et al., Eur. J. Pharmacol. 394: 199-209 (2000)). Chemical inhibitor that was used was furafylline (CYP1A2 inhibitor) and monoclonal antibodies that are inhibitors of CYP2A6, CYP2C9, CYP2C19, CYP2D6, and CYP3A4/5. As shown in FIG. 5, none of these agents significantly affected formation of tritiated water from in HLM, with the exception of the anti-CYP2C9 and anti-CYP2C19 monoclonal antibodies. The antibody directed against CYP2C9, inhibited the reaction by over 80%. The reaction was also inhibited by a monoclonal antibody against CYP2C19, which is known to cross-react with CYP2C9. These results showed that the assay was specific for detecting CYP2C9 activity.

Figure 6:
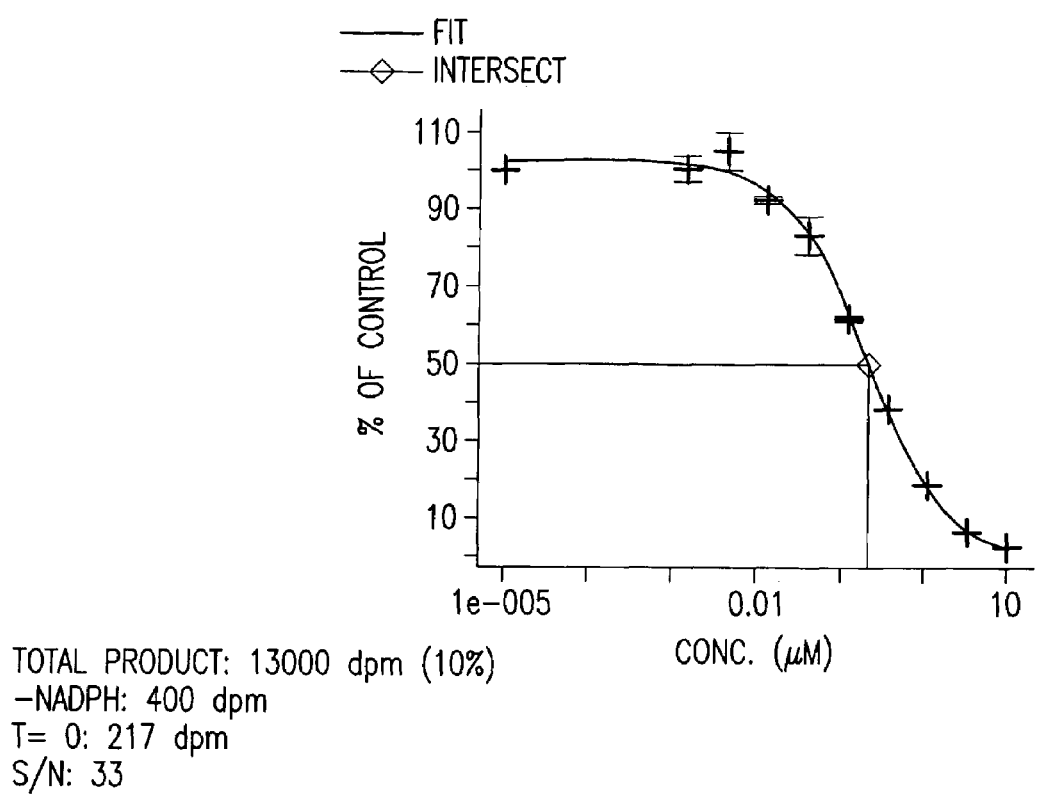
FIG. 6 shows dose-dependent inhibition by sulfaphenazole of tritiated water formation from [4'-$^3$H]-diclofenac in HLM. The assay used 10 μM diclofenac and 134,000 dpm of labeled diclofenac per well. HLM concentration was 0.125 mg/mL.
Figure 7B:
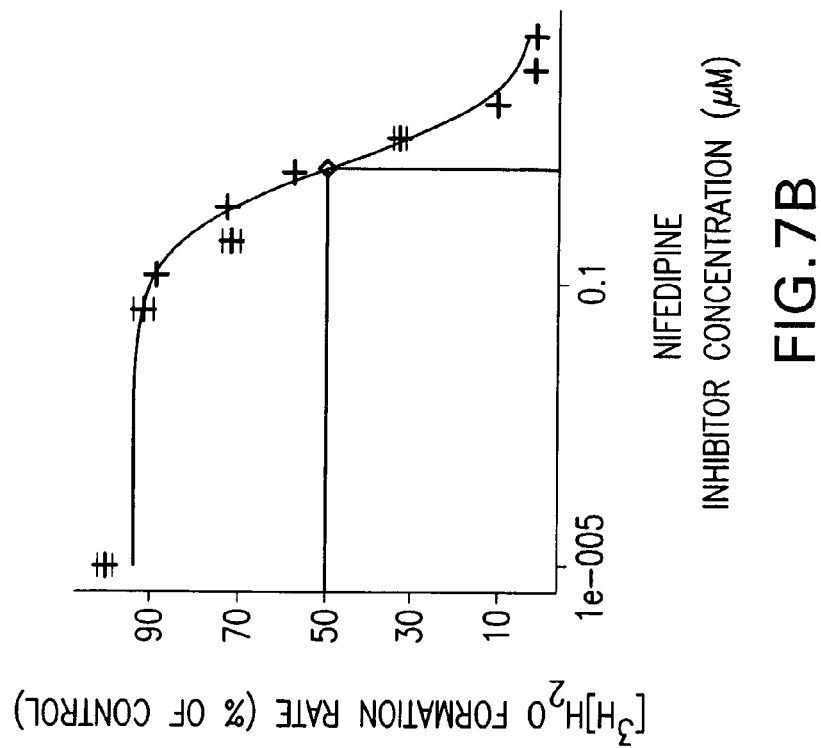
FIG. 7B shows the effect of nifedipine on [$^3$H]—H$_2$O formation from [4'-$^3$H]-diclofenac in human liver microsomes.
Figure 7A:
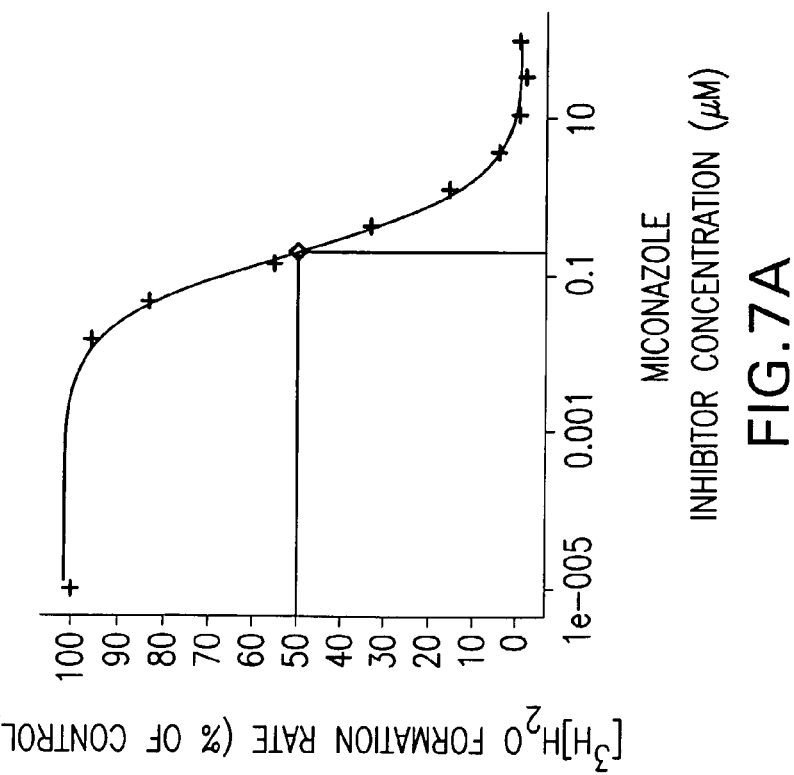
FIG. 7A shows the effect of miconazole on [$^3$H]—H$_2$O formation from [4'-$^3$H]-diclofenac in human liver microsomes.
Figure 7D:
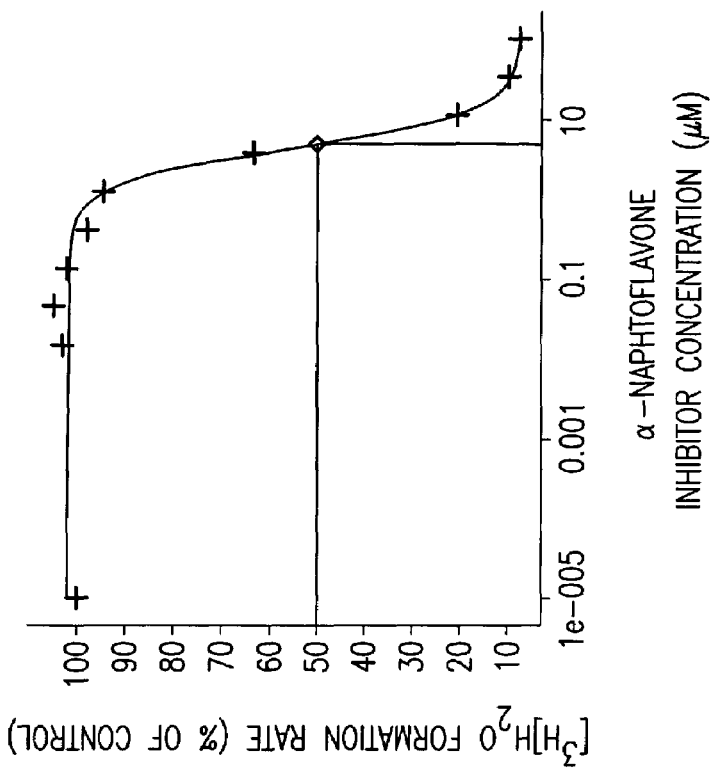
FIG. 7D shows the effect of α-naphtoflavone on [$^3$H]—H$_2$O formation from [4'-$^3$H]-diclofenac in human liver microsomes.
Figure 7C:
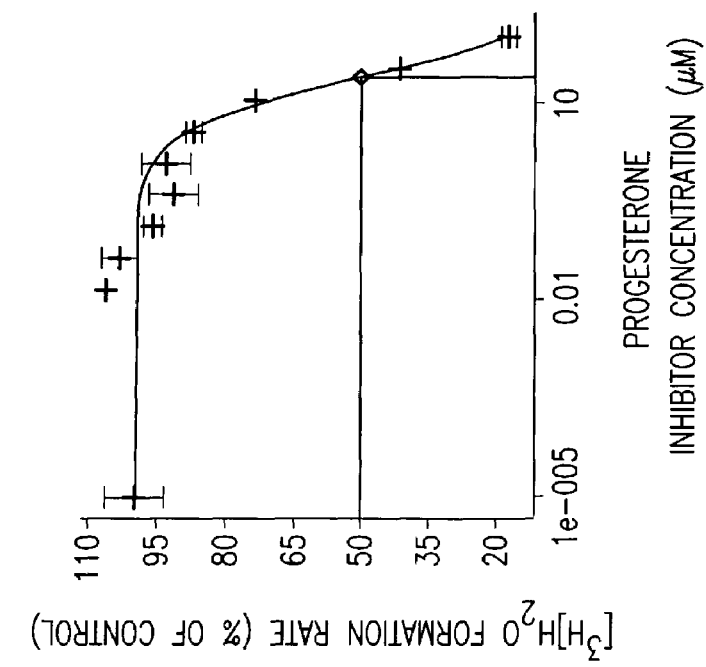
FIG. 7C shows the effect of progesterone on [$^3$H]—H$_2$O formation from [4'-$^3$H]-diclofenac in human liver microsomes.
Figure 7F:
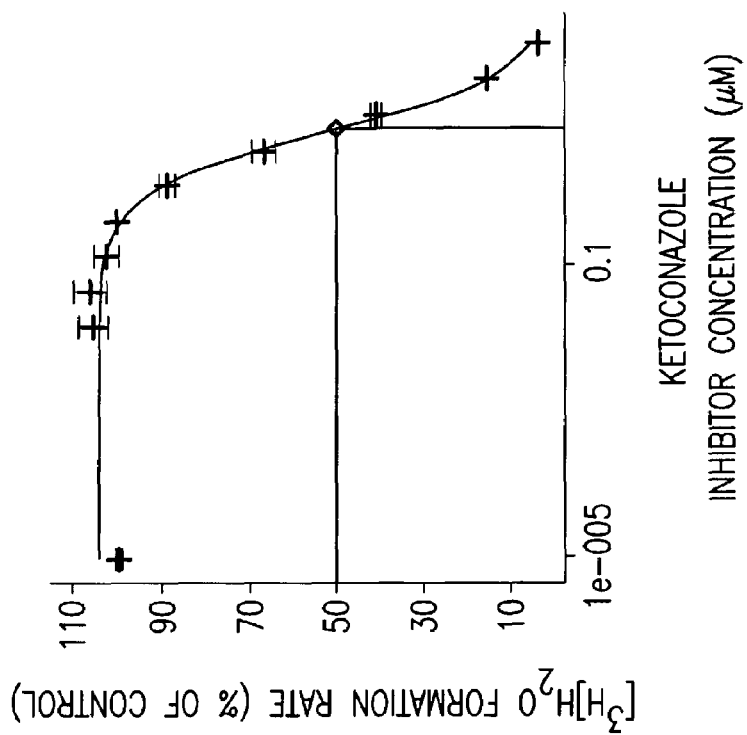
FIG. 7F shows the effect of ketonazole on [$^3$H]—H$_2$O formation from [4'-$^3$H]-diclofenac in human liver microsomes.
Figure 7E:
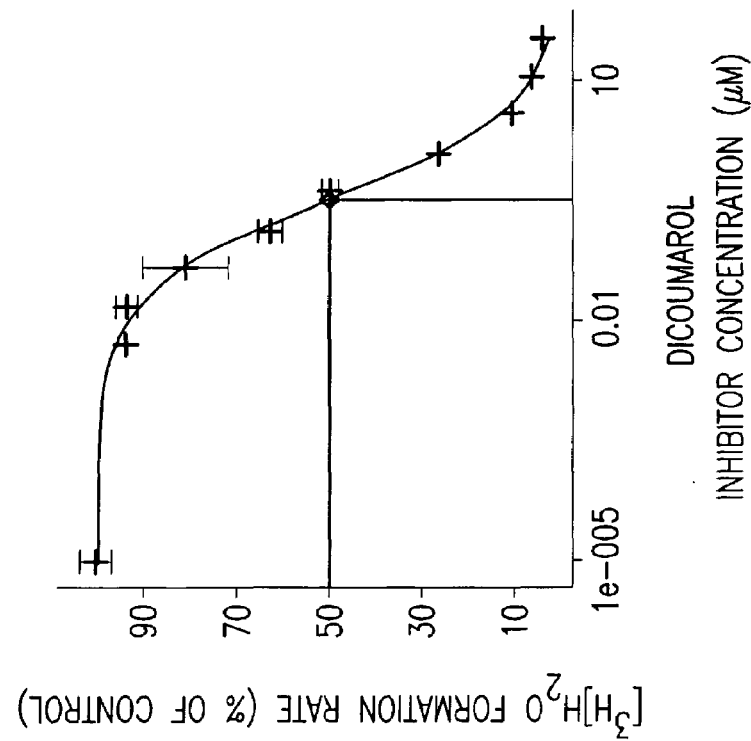
FIG. 7E shows the effect of dicoumarol on [$^3$H]—H$_2$O formation from [4'-$^3$H]-diclofenac in human liver microsomes.

Kinetics of inhibition by CYP2C9 inhibitors. The effect of the CYP2C9 inhibitor sulfaphenazole on NADPH-dependent formation of [$^3$H]—H$_2$O from [4'-$^3$H]-diclofenac in HLM is shown in FIG. 6. Sulfaphenazole inhibited the reaction with an IC$_{50}$ value of 0.2 to 0.3 μM, similar to its IC$_{50}$ value in the conventional diclofenac 4'-hydroxylation assay (HPLC-MS/MS or HPLC-UV) (See Table 1).

Figure 8:
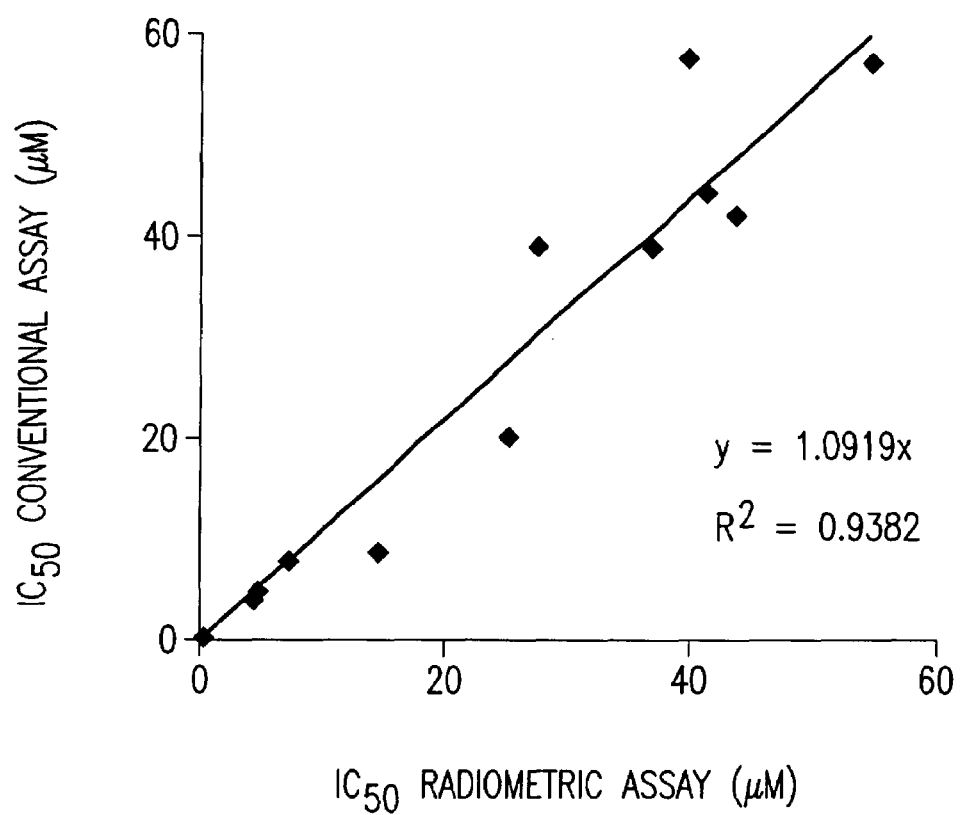
FIG. 8 shows a comparison of IC$_{50}$ values for 16 drugs between radiometric and LC-MS/MS assays by linear regression analysis. Data were from Table 1.

To compare IC$_{50}$ values of several known CYP2C9 inhibitors obtained in the radiometric assay with those obtained by conventional HPLC-mass spectrometric assay, reactions were performed in the absence or presence of different concentrations of known inhibitors. Tritiated water formation and formation of unlabelled reaction product 4'OH-diclofenac were determined in the same reaction mixture. The 4'-OH-diclofenac was quantified by HPLC coupled to triple quadruple mass spectrometric analysis. The effect of some CYP inhibitors (miconazole, nifedipine, progesterone, α-naphtoflavone, dicoumarol, and ketoconazole) on NADPH-dependent formation of [$^3$H]—H$_2$O from [4'-$^3$H]-diclofenac is shown in FIGS. 7A through 7F. IC$_{50}$ values for 18 compounds are summarized in Table 1. IC$_{50}$ values for inhibition of formation of the radiolabelled and non-radiolabelled products were very similar. IC$_{50}$ values differed less than 2-fold in every case. Most importantly, not a single compound out of the 18 tested would have been misclassified as either a strong or weak inhibitor based on the results of the radiometric assay. Linear regression analysis, excluding the 2 compounds with IC$_{50}$ values less than 30 μM, resulted in a line with a slope of 1.09 and a correlation coefficient r$^2$ of 0.938 (FIG. 8). These results demonstrate that the present assay provides a reliable measurement of the potency (IC$_{50}$) of CYP2C9 inhibitors.

A detailed comparison for a large number of compounds of IC$_{50}$ values obtained with a fluorogenic CYP2C9 probe verse diclofenac revealed that the correlation between these assays was not perfect (Cohen et al., op. cit.). For instance, warfarin was an inhibitor of CYP2C9 when probed with diclofenac (IC$_{50}$=22 μM), but not when probed with the fluorogenic substrate MFC. As expected, warfarin inhibited tritiated water formation in the present radiometric assay, with an IC$_{50}$ value of 15 μM. On the basis of the poor correlation between fluorimetric and conventional assays, Cohen and coworkers recommended that screening with fluorogenic probes should be followed up by studies with conventional substrates. The present assay, which combines the advantages of speed, high throughput, and the use of a conventional substrate, circumvents this issue.

TABLE 1

Comparison between IC$_{50}$ values in radiometric vs. conventional assays

| Compound | IC$_{50}$ (μM) radiometric | Conventional | Ratio (radiometric/conventional) |
|---|---|---|---|
| Sulfaphenazole | 0.25 ± 0.02 | 0.26 ± 0.06 | 0.96 |
| Nicardipine | 0.26 ± 0.01 | 0.28 ± 0.03 | 0.93 |
| Fluvastatin | 0.36 ± 0.07 | 0.26 ± 0.07 | 1.38 |
| Dicoumarol | 0.34 ± 0.05 | 0.31 ± 0.08 | 1.10 |
| Miconazole | 0.20 ± 0.02 | 0.13 ± 0.03 | 1.54 |
| Progesterone | 25.2 ± 3.1 | 20.0 ± 4.6 | 1.26 |
| α-Naphthoflavone | 4.5 ± 0.2 | 4.0 ± 0.4 | 1.13 |
| Nifedipine | 4.8 ± 1.2 | 4.6 ± 1.3 | 1.04 |
| Gemfibrozil | 27.7 ± 6.9 | 39.1 ± 7.1 | 0.71 |
| Indomethacin | 54.8 ± 8.1 | 57.0 ± 10.5 | 0.96 |
| Phenylbutazone | 41.4 ± 6.5 | 44.2 ± 2.2 | 0.94 |
| Omeprazole | 43.8 ± 10.4 | 42.3 ± 15.3 | 1.04 |
| Ketoconazole | 7.3 ± 0.8 | 7.8 ± 2.5 | 0.94 |
| Phenytoin | 37.0 ± 3.5 | 38.8 ± 7.8 | 0.95 |
| Ibuprofen | >30 | >30 | na |
| Amiodarone | >100 | >100 | na |
| Mibefradil | 40.0 ± 5.0 | 57.6 ± 9.9 | 0.69 |
| S-Warfarin | 14.6 ± 2.3 | 8.7 ± 3.6 | 1.68 |

The effect of inhibitors on the formation rate of [$^3$H]-H$_2$O (radiometric)and 4'-hydroxydiclofenac (conventional) was determined in the same reaction mixture. 4'-hydroxydiclofenac was quantified using LC-MS/MS. IC$_{50}$ values were calculated from full inhibition curves with at least 8 concentration points. Data are mean values ± SEM, n = 2.

EXAMPLE 3

Determination of the kinetic tritium isotope effect. $^T$V/K, the kinetic isotope effect on the V/K ratio, was determined according to the formula (Northrop, Meth. Enzymol. 87: 607-625 (1982))

$$^TV/K = \frac{\log(1-f)}{\log\left(1-f\frac{SA_P}{SA_0}\right)} \quad \text{equation 1}$$

where f is the fractional conversion of substrate to product, SA$_0$ is the initial specific radioactivity of labeled substrate, and SA$_P$ is the specific radioactivity of product. At low values of f (<5%), such as those observed in the present experiments, this expression reduces to (Northrop, ibid.):

$$^TV/K \approx \frac{SA_0}{SA_P} \quad \text{equation 2}$$

Calculation of the apparent rate of formation of unlabelled product from tracer competition experiments. When assays are performed using a fixed amount of [4'-$^3$H]-diclofenac and varying concentrations of unlabelled diclofenac, the velocity of formation of unlabelled product, v, is given by:

$$v = v^*/SA_P \quad \text{equation 3}$$

where v* is the velocity of formation of tritiated water. Substituting from equation 2, we obtain:

$$v = v^* \times (^TV/K)/SA_0 \quad \text{equation 4}$$

Defining v' as the velocity of formation of unlabelled product divided by the kinetic isotope effect, i.e.

$$v' = v/(^T V/K) \quad \text{equation 5}$$

we obtain $$v' = v^*/SA_0 \quad \text{equation 6}$$

Without using the known $^T V/K$ ratio (which would be tautological, since it was derived from $SA_P$), v', the apparent formation rate of unlabelled product, can be calculated. When plotted against the substrate concentration, S, and fitted to the Hill equation (equation 7), $V'_{max}$, $S_{50}$, the substrate concentration at 50%, and n, the Hill coefficient, can be derived.

$$v' = \frac{V'_{max} \times S^n}{S_{50}^n + S^n} \quad \text{equation 7}$$

where $V'_{max} = V_{max}/(^T V/K)$, i.e. the apparent maximal rate of product formation.

Results

Figure 9:
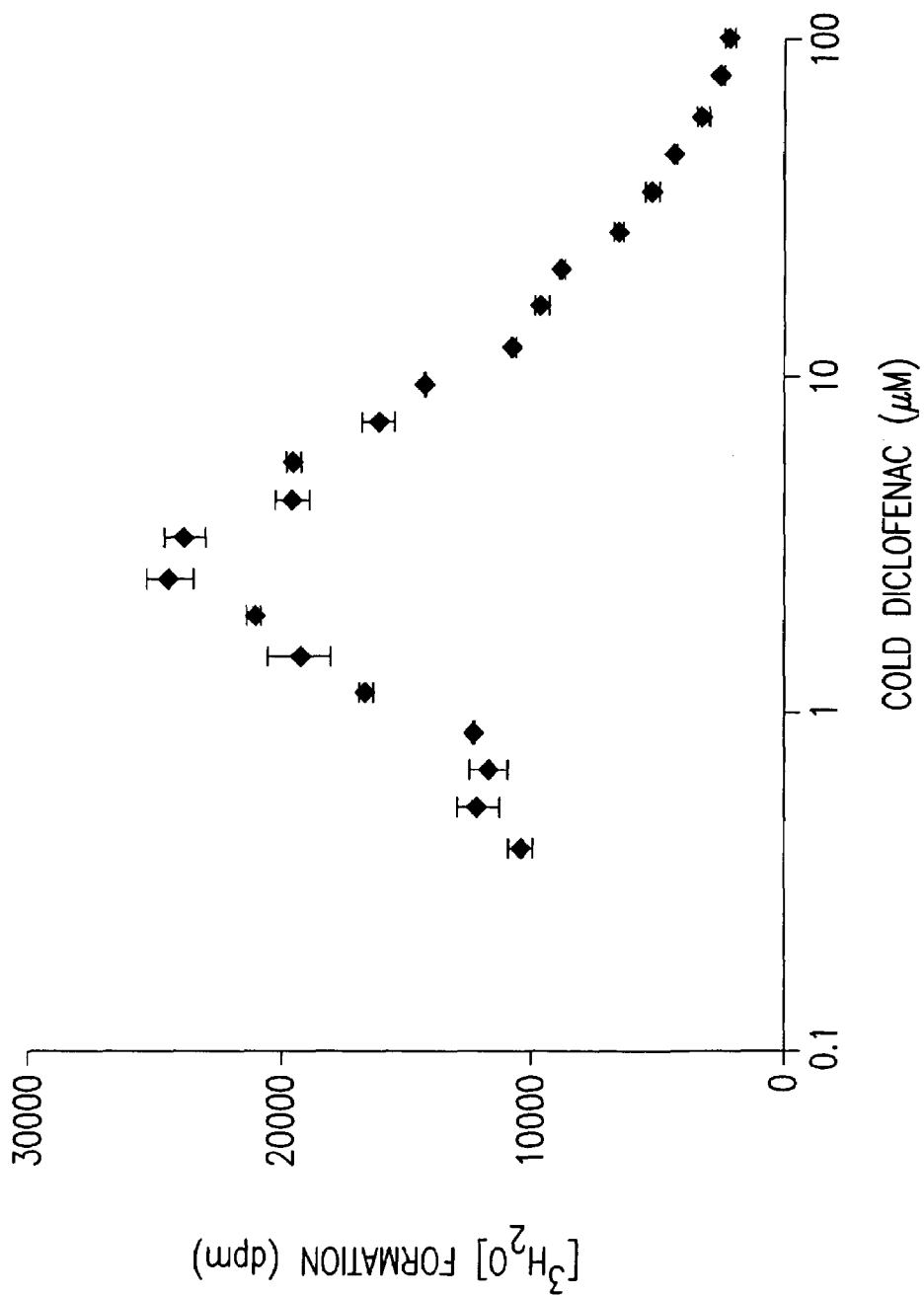
FIG. 9 shows the effect of increasing concentrations of unlabelled diclofenac on tritiated water formation from [4'-$^3$H]-diclofenac in HLM.

Competition between radiolabelled and unlabelled diclofenac. The effect of unlabelled diclofenac on the formation of tritiated water in HLM is depicted in FIG. 9. The curve displays a "low dose hook", i.e. product formation rate increased with increasing concentration of unlabelled substrate, reached a peak at a diclofenac concentration of ~3 µM, and then decreased. This effect is characteristic for positive coöperative ligand displacement interactions (De Lean and Rodbard, Recept.: Compr. Treatise 1: 143-192 (1979)). The reason for the increased formation of tritiated product is that at low substrate concentrations, the reaction velocity of a positively cooperative enzyme increases more than dose-proportionally with increasing substrate concentration. Note that CYP2C9-mediated diclofenac 4'-hydroxylation has not previously been reported to display cooperative kinetics. This is likely due to the fact that cooperativity is revealed by the sensitive nature of the present radiochemical assay and is observed only at very low substrate concentrations, while the classical assay is usually performed at higher substrate concentrations. However, positive coöperativity and heteroactivation has been reported for other CYP2C9 substrates, such as dapsone (Korzekwa et al., Biochemistry 37: 4137 (1998); Hutzleretal., Arch. Biochem. Biophys. 410: 16 (2003); Hummel et al. Biochemistry 43: 7207 (2004); Egnell et al., J. Pharmacol. Exp. Ther. 307: 878 (2003)).

Figure 10:
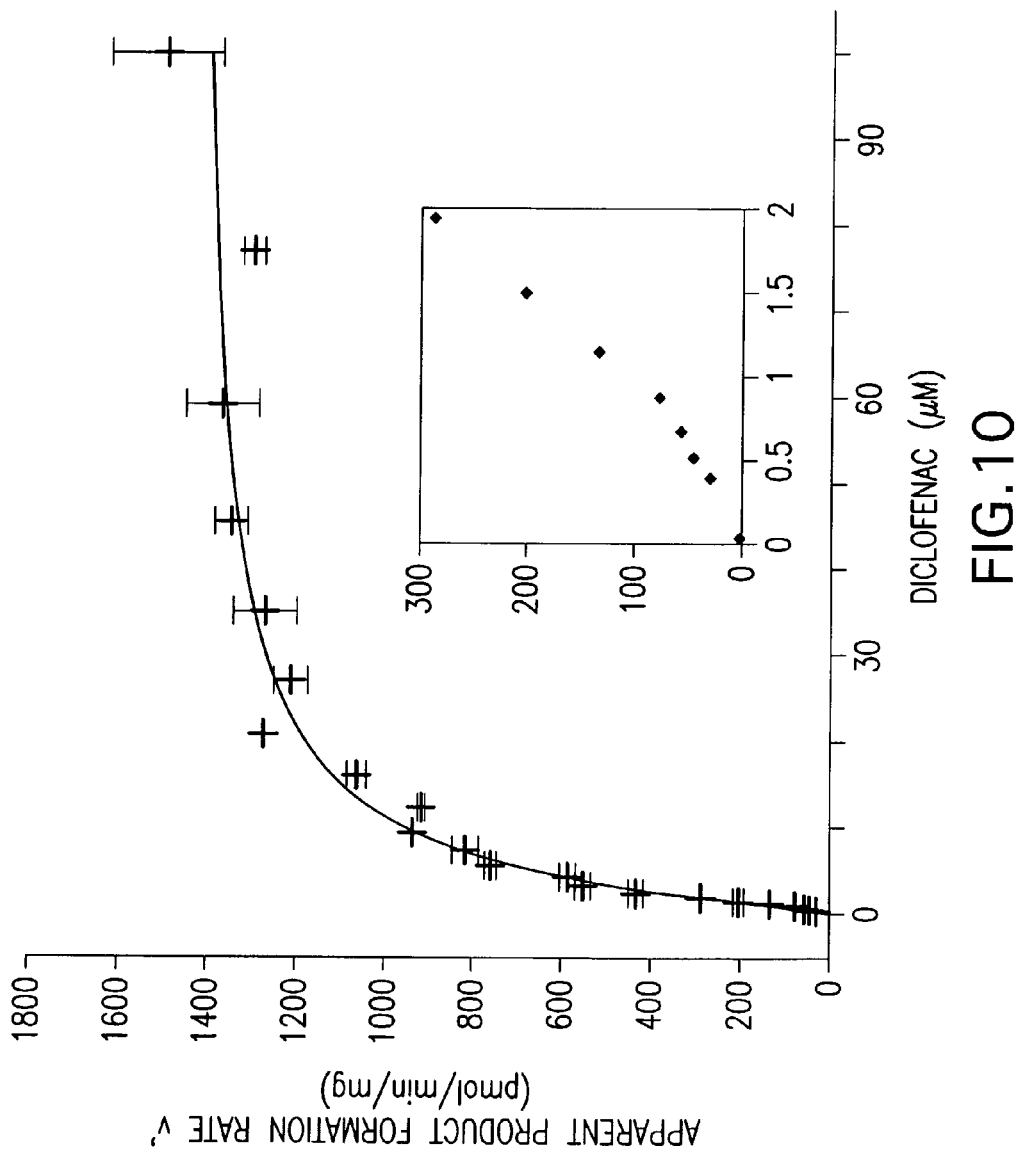
FIG. 10 shows the dependence of v' on total substrate concentration. The term v', defined as described in Example 3, was calculated from the product counts shown in FIG. 8. Data were fitted to the Hill equation by nonlinear regression analysis.

Since [4'-$^3$H]-diclofenac is used as an isotopic tracer, the formation rate of tritiated water (v*) is representative of that of unlabelled product, namely water derived from 4'-hydroxylation of diclofenac (which is formed stoichiometrically with 4'-hydroxydiclofenac). The dependence of v* on substrate concentration (S) can be used to obtain information about the dependence on substrate concentration of the unlabelled product, even if the latter is not measured directly. We define v', the apparent formation rate of unlabelled product, as the formation rate of unlabelled product (v) divided by the kinetic isotope effect (See Experimental section above). As depicted in FIG. 10, the curve of v' vs. S could be fitted to the Hill equation, with $S_{50}$=6.8±1.0 µM, n=1.15±0.05, and $V'_{max}$=1.5±0.1 nmol/min/mg (average ±SEM, n=2). The Hill coefficient was slightly greater than 1, suggesting weak positive cooperativity. Indeed, at low substrate concentrations, a sigmoidal relationship was observed between v' and S, as depicted in the inset of FIG. 10.

Figure 11:
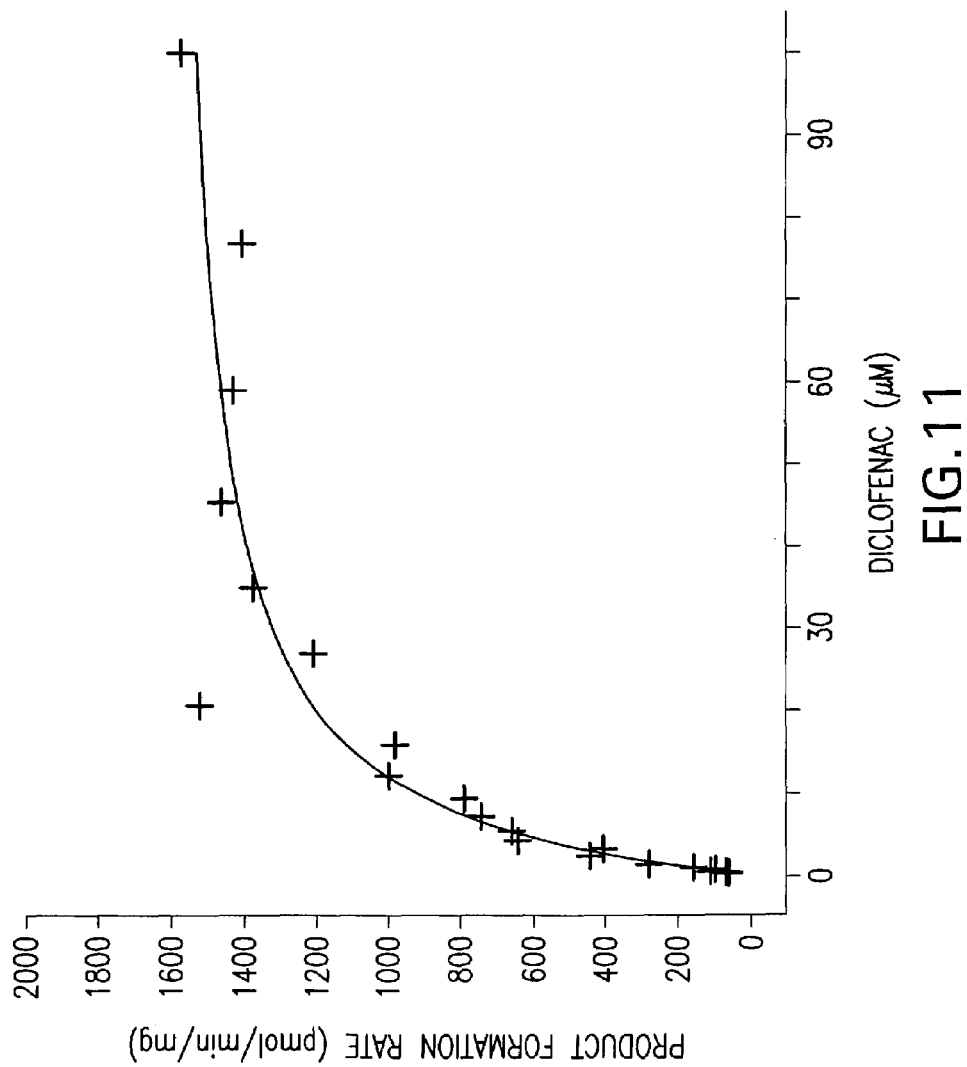
FIG. 11 shows the dependence of the velocity of formation of 4'-hydroxydiclofenac on total substrate concentration. Data were fitted to the Hill equation by nonlinear regression analysis.

The kinetics of 4'-hydroxydiclofenac formation is depicted in FIG. 11. The reaction had an $S_{50}$ 6.2±0.9 µM, $V_{max}$ of 1.3±0.3 nmol/min/mg protein, and Hill coefficient of 1.1±0.1 (average ±SEM, n=3). Note that the ratio between $V'_{max}$ and $V_{max}$ is 0.9, indicating absence of a significant kinetic isotope effect.

EXAMPLE 4

This example illustrates the use of the present invention to determine and quantify the enzymatic activity and the effect of CYP2C9 inhibitors on intact hepatocytes.

Hepatocytes were isolated from fresh human livers and cryopreserved in liquid nitrogen according to established protocols (See for example, Hengstler et al., Drug Metab. Rev. 32: 81-118 (2000); Ferrini et al., Methods Mol. Biol. 107: 341-52 (1998)). Cells were thawed, plated at a density of 150,000 cells/cm$^2$ in collagen-coated 24-well or 96-well culture plates and maintained at 37° C. in a humidified atmosphere of 5% $CO_2$ in hepatocyte culture medium (HCM) (Dich and Grunnet, in Methods in Molecular Biology, Vol. 5: Animal Cell Culture (Pollard and Walker, eds) pp. 161-176, Humana Press, Clifton, N.J. (1989)) supplemented-with ITS+ (Collaborative Research, Waltham, Mass.). Cells were incubated with 10 µM unlabelled diclofenac, 500,000 dpm/mL of [4'-$^3$H]diclofenac, in the absence or presence of the CYP2C9 inhibitor sulfaphenazole (at 10 µM). After different times, aliquots of the incubation medium were loaded onto individual wells of preconditioned 30 mg OASIS plates, which were washed two times with 200 µL of water. For each well, the flow-through was combined with the water washes and counted in a beta-counter after addition of scintillation fluid.

Figure 12:
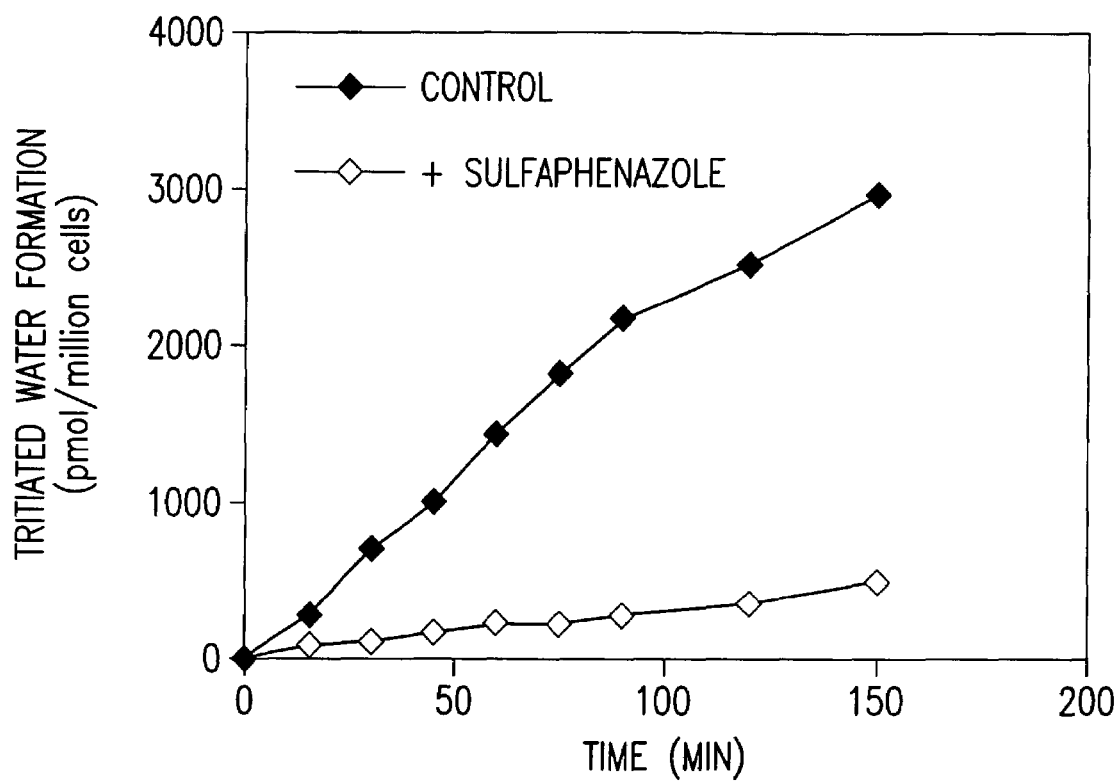
FIG. 12 shows formation of tritiated water from [4'-$^3$H]-diclofenac in human hepatocytes in the presence or absence of 10 μM sulfaphenazole.

As shown in FIG. 12, tritiated water was formed in a time-dependent manner from [4'-$^3$H]diclofenac in human hepatocytes, and the reaction was almost totally inhibited by the CYP2C9 inhibitor sulfaphenazole. These results demonstrate that the assay can be used to determine the activity of CYP2C9 and the effect of CYP2C9 inhibitors in intact hepatocytes.

EXAMPLE 5

This example illustrates the use of the present invention to identify analytes that induce CYP2C9 expression.

Cryopreserved human hepatocytes from two different donors are obtained. Cells (ca. 320,000) are plated in 24-well collagen-coated culture plates and maintained at 37° C. in a humidified atmosphere of 5% $CO_2$, 95% air, in hepatocyte culture medium (HCM) (Dich and Grunnet, ibid.) supplemented with ITS+ (Collaborative Research, Waltham, Mass.). Twenty-four hours later, the culture medium for each well of cells was removed, fresh HCM with ITS was added, and cells were treated with either vehicle (control), an inducer of CYP2C9 expression such as riframpicin, dexamethasone, or phenobarbital (positive control), or analyte being tested for ability to induce CYP2C9 activity for 48 hours. CYP2C9 enzyme activity was then determined as follows.

For each well, the medium is removed and the cells incubated in 0.5 mL of Hank's balanced salt solution (HBSS) containing 10 mM Hepes, pH 7.4, 60 µM unlabelled diclofenac, and ca. 200,000 dpm of [4'-$^3$H]-diclofenac for 1 hour at 37° C. For each, parallel incubations are performed in the presence of an inhibitor such as sulfaphenazole to ascertain that enzyme activity was specifically mediated by CYP2C9. The incubation medium is loaded onto individual wells of preconditioned 30 mg OASIS plates, which have been washed two times with 200 μL of water. For each well, the flow-through is combined with the water washes and counted in a beta-counter after addition of scintillation fluid. The presence of tritiated water compared to controls that do not contain an inducer of CYP2C9 expression indicates that the analyte is an inducer of CYP2C9 expression.

To confirm that the analyte is induced CYP2C9 expression, 4'-hydroxydiclofenac is eluted from the OASIS plates with 1 mL of methanol, dried under $N_2$, and reconstituted in 200 μL of 50% acetonitrile/water (50:50) containing 0.1% of formic acid. Aliquots are injected into an HPLC-MS/MS system for quantification of 4'-hydroxydiclofenac. Quantification is based on comparison of peak areas with those of a standard curve that is treated and extracted exactly like unknown samples.

EXAMPLE 6

This example shows an example of how to perform a time-dependent CYP2C9 assay using HLM.

The preincubation step is performed as follows. Preincubation mixtures containing about 30 μL HLM (3.3 mg/ml of protein, preferred final concentration 2 mg/mL; range 0.1 to 5 mg/mL), 1μL of test analyte (dissolved in 35% DMSO, 65% Methanol), 9 μL of assay buffer (0.1 M potassium phosphate, pH 7.6). Preincubations are started by adding 10 μL of NADPH regenerating system (5 mM NADPH, 25 mM Glucose-6-phosphate, 17 mM $MgCl_2$, 5 U/mL Glucose-6-phosphate dehydrogenase, in assay buffer). Preincubations are started at different times in reverse order (longest preincubation was started first, shortest preincubation was started last). Mixtures are preincubated in a shaking water bath for 0-30 minutes at 37° C.

Determination of remaining activity is as follows. The second incubation is started by about 10-fold dilution of the preincubation mixtures with 450 μL of assay buffer containing [4'-$^3$H]-diclofenac) (about 800,000 dpm), 30 to 100 μM unlabelled diclofenac and 1 mM NADPH. Incubations are performed in a shaking water bath for 10 min at 37° C. Reactions are stopped by addition of about 50 μL of 1N HCl. Plates are centrifuged at room temperature at 2800 rpm for 15 minutes. About 300 μL of supernatant are loaded on a preconditioned 30 mg OASIS plate. The flow-through is collected and aliquots of 120 μL are transferred into 96 well scintillation counting plates (Packard). 180 μL of MICROSCINT 40 scintillation fluid is added and plates are sealed, shaken, and counted in a Packard TOPCOUNT scintillation counter.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for identifying an analyte that inhibits activity of cytochrome P450 isoform 2C9 (CYP2C9), which comprises:
   (a) providing an aqueous mixture comprising CYP2C9, tritium-labeled diclofenac labeled with tritium at the 4' position ([4'-$^3$H]-diclofenac), NADPH, and the analyte;
   (b) incubating the aqueous mixture for a time sufficient for the CYP2C9 activity to hydroxylate the tritium-labeled diclofenac at the 4' position;
   (c) removing the CYP2C9 from the aqueous mixture;
   (d) applying the aqueous mixture to a sorbent which preferentially binds non-polar compounds to remove the tritium-labeled diclofenac from the aqueous mixture; and
   (e) measuring amount of the tritium in the aqueous mixture of step (d) wherein a decrease in the amount of the tritium in the aqueous mixture compared to the amount of tritium in the aqueous mixture from a control mixture comprising CYP2C9, diclofenac labeled with tritium in the 4' position of the phenyl ring, and NADPH, and not the analyte identifies the analyte as an inhibitor of the CYP2C9.

2. The method of claim 1 wherein the sorbent is selected from the group consisting of water-wettable polymers formed by copolymerizing at least one hydrophilic monomer and at least one lipophilic monomer in a ratio sufficient for the polymer to be water-wettable and effective at retaining organic solutes thereon, silica substrates comprising a non-polar group bonded to the silica substrate, and activated charcoal.

3. The method of claim 2 wherein the sorbent is poly (vinylbenzene-co-N-vinylpyrrolidone).

4. The method of claim 1 wherein the diclofenac labeled at the 4' position is produced by providing a mixture of 2-iodophenyl acetic acid and 2,6-dicloro 4-bromoaniline; incubating the mixture in the presence of a copper catalyst to produce 2-[(2,6-dichloro, 4-bromophenyl)amino]phenylacetic acid; and, incubating the 2-[(2,6-dichloro, 4-bromophenyl)amino]phenylacetic acid with tritium in the presence of a palladium catalyst to produce the diclofenac labeled at the 4' position.

5. The method of claim 1 wherein the aqueous mixture further comprises an NADPH regenerating system.

6. The method of claim 1 wherein the CYP2C9 is provided in microsomes.

7. The method of claim 6 wherein the microsomes are human liver microsomes.

8. The method of claim 6 wherein the microsomes are produced from cells selected from the group consisting of mammalian and insect cells, wherein the cells include a vector expressing the CYP2C9.

* * * * *